(12) United States Patent
Razavi-Shirazi et al.

(10) Patent No.: US 9,551,013 B2
(45) Date of Patent: *Jan. 24, 2017

(54) CYCLIC BIOCONVERSION PROCESSES AND BIOREACTOR ASSEMBLIES

(71) Applicant: Microvi Biotech, Inc., Hayward, CA (US)

(72) Inventors: Fatemeh Razavi-Shirazi, Hayward, CA (US); Mohammad Ali Dorri, Milpitas, CA (US); Ameen Razavi, Fremont, CA (US)

(73) Assignee: MICROVI BIOTECH, INC., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/407,777

(22) PCT Filed: Jun. 14, 2013

(86) PCT No.: PCT/US2013/046029
§ 371 (c)(1),
(2) Date: Dec. 12, 2014

(87) PCT Pub. No.: WO2013/188852
PCT Pub. Date: Dec. 19, 2013

(65) Prior Publication Data
US 2015/0167024 A1    Jun. 18, 2015

Related U.S. Application Data

(60) Provisional application No. 61/689,921, filed on Jun. 15, 2012, provisional application No. 61/849,725, filed on Feb. 1, 2013.

(51) Int. Cl.
*C12P 7/04* (2006.01)
*C12M 1/00* (2006.01)
(Continued)

(52) U.S. Cl.
CPC ............... *C12P 7/04* (2013.01); *C12M 23/34* (2013.01); *C12M 25/20* (2013.01); *C12M 27/24* (2013.01); *C12M 29/18* (2013.01); *C12N 11/00* (2013.01)

(58) Field of Classification Search
CPC ..................................................... C12M 25/14
See application file for complete search history.

(56) References Cited

U.S. PATENT DOCUMENTS 7,923,227 B2    4/2011   Hickey et al.
7,977,089 B2    7/2011   Wikswo et al.
(Continued)

FOREIGN PATENT DOCUMENTS

EP    0465131 A2    1/1992
WO    00/01803 A1    1/2000

OTHER PUBLICATIONS

International Search Report dated Nov. 22, 2013 corresponding to International Patent Application No. PCT/US13/46029, 2 pages.
(Continued)

*Primary Examiner* — Rosanne Kosson
(74) *Attorney, Agent, or Firm* — Dentons US LLP

(57) ABSTRACT

Bioconversion processes are disclosed in which biocatalysts including microorganisms or isolated enzymes that are substantially irreversibly retained in the interior of an open, porous, highly hydrophilic polymer are cycled between at least two different fluid media for the bioconversion of one or more substrates to one or more bioproducts. The processes are particularly attractive for using gas phase or using liquid feedstocks containing the substrate.

8 Claims, 3 Drawing Sheets

(51) Int. Cl.
  *C12M 1/12* (2006.01)
  *C12M 1/08* (2006.01)
  *C12N 11/00* (2006.01)

(56) References Cited

U.S. PATENT DOCUMENTS

| | | |
|---|---|---|
| 8,062,873 B2 | 11/2011 | Tsai et al. |
| 8,198,055 B2 | 6/2012 | Datta et al. |
| 2009/0104676 A1 | 4/2009 | Tsai |
| 2010/0105116 A1 | 4/2010 | Datta et al. |
| 2010/0294642 A1 | 11/2010 | Datta et al. |
| 2011/0183390 A1 | 7/2011 | Hickey et al. |
| 2012/0070888 A1 | 3/2012 | Tsai et al. |

OTHER PUBLICATIONS

Partial Supplementary European Search Report, dated Nov. 18, 2015 corresponding to European Patent Application No. 13803990. 4, 7 pages.

International Preliminary Report on Patentability dated Dec. 16, 2014 corresponding to International Patent Application No. PCT/US2013/046029, 7 pages.

CYCLIC BIOCONVERSION PROCESSES AND BIOREACTOR ASSEMBLIES

CROSS-REFERENCE TO PRIOR APPLICATIONS

This application is a National Stage of PCT/US2013/046029, filed Jun. 14, 2013, and designating the United States (published on Dec. 19, 2013, as WO 2013/188852 A1), which claims priority under 35 U.S.C. §119 to U.S. Provisional Patent Application Nos.: 61/689,921, filed on Jun. 15, 2012, and 61/849,725, filed on Feb. 1, 2013, each hereby expressly incorporated by reference in its entirety and each assigned to the assignee hereof.

FIELD OF THE INVENTION

This invention pertains to bioconversion processes in which biocatalysts comprising microorganisms or isolated enzymes that are substantially irreversibly retained in the interior of an open, porous, highly hydrophilic polymer are cycled between at least two different fluid media for the bioconversion of one or more substrates to one or more bioproducts.

BACKGROUND

Metabolic processes have long been proposed for anabolic and catabolic bioconversions. Microorganisms of various types have been proposed for these bioconversions and include bacteria and archaea, both of which are prokaryotes; fungi; and algae. Metabolic processes are used by nature, and some have been adapted to use by man for millennia for anabolic and catabolic bioconversions ranging from culturing yogurt and fermentation of sugars to produce alcohol to treatment of water to remove contaminants. Metabolic processes offer the potential for low energy consumption, high efficiency bioconversions in relatively inexpensive processing equipment and thus may be and are often viable alternatives to chemical synthesis and degradation methods. Often anabolic processes can use raw materials that are preferred from a renewable or environmental standpoint but are not desirable for chemical synthesis, e.g., the conversion of carbon dioxide to biofuels and other bioproducts. Catabolic bioconversions can degrade substrates and have long been used for waste water treatment. Considerable interests exist in improving metabolic processes for industrial use and expanding the variety of metabolic process alternatives to chemical syntheses and degradations.

In some instances difficulties can occur where it is not desirable to contact the gaseous or liquid feedstock containing the substrate with the aqueous medium containing the microorganism for the metabolic process. For example, the gaseous or liquid feedstock may contain components that could build up in the aqueous medium such as solids; or a liquid feedstock containing the substrate may result in dilution of the aqueous medium requiring large reactor sizes. Additionally, the feedstock may not be aqueous or may contain two liquid phases. Introducing a gas phase feedstock into an aqueous medium may require compression of the gaseous medium in order to overcome the hydraulic head of the aqueous medium resulting in capital and operating expense.

Especially for substrates that are sparingly soluble in water, economic viability of commercial-scale bioconversion processes will not only depend upon the bioconversion rate and efficiency but also on the rate of mass transfer of the substrate from the gas phase to the aqueous phase. The mass transfer rate will be reflected, in part, by the surface area between the gas and liquid phases and the duration of contact. Accordingly, proposed bioreactors trend toward the use of smaller bubbles of gas and contact times sufficient to enable a desired amount of mass transfer of gas into the aqueous phase to be achieved both of which can add to capital and operating expenses. The challenges faced are even greater where the substrate is in a low concentration in the gaseous fluid.

Bioreactor designs have been proposed for treating gas phase feedstocks where the microorganisms are contained on a solid structure. Typically these reactors maintain the microorganisms and the solid structure externally wet in order to maintain the microorganism.

Birdwell, et al., in U.S. Pat. No. 5,409,823 disclose an apparatus for removing pollutants from air by spraying a microbial laden liquid into incoming polluted air in a wet plenum chamber having a liquid level therein. The air passing out of the wet plenum chamber enters a wet sill chamber having a filtration medium that is sprayed with liquid laden microbial agents to provide further dwell time. The patentees suggest that their process is useful for the removal of volatile organic compounds, air toxins and odors.

Apel in U.S. Pat. No. 5,795,751 discloses a biofilter for the removal of nitrogen oxides from contaminated gases under aerobic conditions. The biofilter is a porous, organic filter bed, preferably wood compost. At column 3,lines 33 et seq., the patentees state that moisture lost can be replenished periodically by the addition of a liquid, such as a buffer solution, to the compost.

Barshter, et al., in U.S. Pat. No. 5,821,114, disclose a biofilter using modular panels where contact between the gas and the microbial population on the filter removes contaminants. The patentees propose the use of the filter for the removal of hydrocarbons, reduced sulfurs, ammonia, and the like. At column 3, lines 57, et seq., the patentees state that moisture is preferably added periodically by means of sprinklers or perforated hose.

Breckenridge in U.S. Pat. No. 6,117,672 discloses a moving bed biofilter and condenser for flue gas pollutant removal and collection. In his process, a moving belt conveying a wet mat of chopped biomass impregnated with bacteria that feed on nitrogen oxides is used. The gas is passed through the belt.

Ren, et al., in U.S. Published Patent Application No. 2012/0208262 disclose improved biotrickling filters for treating waste gas. Waste gases pass through a packed bed which is maintained wet using sprays. The apparatus involves changing the direction of the gas flow.

Another trickle bed is discussed by Jiang, et al., in *Nitrogen oxide removal from flue gas with a biotrickling filter using Pseudomonas putida*, Journal of Hazardous Materials, 164, pages 432-441 (2009). The authors noted several practical problems with trickle bed bioreactors. First, the pressure drop through the bed can be material in commercial units where using the smaller diameter supports (about 2 to 3 millimeters in diameter) to provide high surface area per unit volume. Second, microbial contamination can occur. Third, biofilm build up can occur that can cause failure of the system. Fourth, the microorganisms, and sought biofilms, can be washed from the surface of the supports thereby making backwashing difficult. And fifth, start-up of bioreactors to enhance adhesion of the microorganisms on the support may require a laborious empirical approach.

A yet another approach is to use biofilm membranes where the gas to be treated is maintained on one side of the membrane and an aqueous medium is provided on the other side. Microorganisms may form a biofilm on aqueous medium side of the membrane. A driving force provides for the permeation of the sought substrate through the membrane where bioconversion occurs. Energy is required for the transport of the substrate through the membrane, which has to have sufficient strength to provide physical integrity. Moreover, the formation of excess biofilms or microbial contamination can adversely affect the performance of the biofilm membranes.

Accordingly improved processes are sought for bioconverting substrate where the feedstock supplying the substrate presents challenges to bioconversions where the microorganisms or enzymes need to be retained in an aqueous medium.

SUMMARY

In accordance with the processes of this invention, certain biocatalyst compositions that contain microorganisms or isolated enzymes (both referred to as bioactive materials) are cycled between conditions for contact with feedstock containing substrate and conditions facilitating metabolic activity. These biocatalyst compositions have properties particularly beneficial to this cycling.

The biocatalysts have a high Hydration Expansion Volume (HEV) and are hydrated and thus physically protect the bioactive material from dehydration. Hence, it is not necessary that the feedstocks be aqueous or that aqueous medium be supplied during the contact between the biocatalyst and the feedstock. Thus, the biocatalysts can be used with a gas phase containing substrate and liquid phase containing substrate that are less suitable for metabolic activity. The cycling can enable in some instances a more concentrated bioproduct stream to be obtained. As stated above, the bioactive materials are retained in the interior of the biocatalysts and thus are not a source of debris that can foul the biocatalyst. Further, the biocatalysts can be moved without damage to the bioactive materials therein. Since the bioactive materials are contained in the interior of the biocatalyst, high densities of bioactive material can be achieved in a bioreactor without operational problems such as high viscosity media that occur with high, suspended cell densities. Thus high rates of bioconversion per unit volume of bioreactor can be achieved.

The biocatalyst sorbs substrate for mass transfer to the bioactive material in the interior of the biocatalyst. The sorption provides the ability to decouple up-take of substrate and metabolic conversion of substrate and decouple the presence of additives such as carbon source, other nutrients, promoters, inducers, co-metabolites and the like from the feedstock.

In its broad aspect, the processes of this invention for bioconverting substrate in a fluid feedstock to bioproduct comprise:

a. contacting said feedstock with biocatalyst containing bioactive material capable of bioconverting said substrate to bioproduct for a time sufficient for the up-take of a least a portion of said substrate into the biocatalyst and provide a loaded biocatalyst, said biocatalyst comprising a solid structure of hydrated hydrophilic polymer defining an interior structure having a plurality of interconnected major cavities having a smallest dimension of between about 5 and 100 microns and an HEV of at least about 1000, preferably at least about 5000, and bioactive material substantially irreversibly retained therein;

b. thereafter contacting the biocatalyst with an aqueous medium providing conditions to facilitate metabolic activity; and c. thereafter using said biocatalyst in step (a), wherein the loaded biocatalyst in step (a) is maintained in at least one of steps (a) and (b) under metabolic conditions for a time sufficient to bioconvert at least a portion of the substrate to bioproduct.

The bioproduct may be recovered in either or both of steps (a) and (b) or an additional product recovery step may be used. In some instances, the bioproduct may be retained in the biocatalyst such as could occur in a metabolic reduction of soluble metal compound to form a metal-containing solid. The processes of this invention may be batch, semi-batch, but are particularly attractive for continuous operations as the bioactive material is retained in a solid biocatalyst. The processes of this invention may be conducted by retaining the biocatalyst in a bioreactor and changing the media contacting the biocatalyst to effect the cycling or by moving the biocatalyst between bioreactors. As can be readily appreciated, the processes of this invention can include additional steps, e.g., for washing the biocatalyst, recovery of bioproduct, addition of one or more nutrients, conducting additional bioconversion steps, and the like.

The subsequent contact of the biocatalyst with aqueous medium in step (b) can serves to facilitate the bioconversion. By facilitating the bioconversion, it is meant that one or more of the following occur: more time for the bioconversion; more favorable temperatures for the bioconversion; change in redox conditions; presence of a food source and other nutrients, or the presence of co-substrates, inducers, promoters or co-metabolites; supply of energy including, but not limited to electricity, actinic radiation, or other electromagnetic energy; removal of bioproduct or other metabolites or toxins sorbed or generated during contact with the feedstock; and the presence of a chemical agent or other bioactive materials to convert a bioproduct to another product which may be the sought product or intermediate or may facilitate recovery of the bioproduct.

One preferred aspect of this invention pertains to gas phase bioconversion processes. This aspect pertains to processes for bioconversion of substrate contained in a gas phase to bioproduct comprising:

a. continuously contacting the gas phase with biocatalyst having bioactive material substantially irreversibly retained therein, preferably for a time sufficient to provide a steady-state mass transfer to and bioconversion of substrate, wherein:

i. said biocatalyst has an interior defined by a solid structure comprised of hydrated, hydrophilic polymer which contains a plurality of interconnected major cavities having a smallest dimension of between about 5 and 100 microns, and said biocatalyst has a Hydration Expansion Volume of at least about 1000, preferably at least about 10,000, percent, and ii. said biocatalyst contains therein an aqueous medium;

b. cycling at least a portion of biocatalyst of step (a) to at least one immersion step in an aqueous medium for a time sufficient to substantially fully hydrate the biocatalyst, and preferably, where the biocatalyst comprises microorganisms, at least one of said immersion steps comprises nutrients for the microorganisms and said immersion being for a time sufficient to provide nutrients in said biocatalyst;

c. separating the biocatalyst from the at least one immersion step; and d. passing at least a portion of the separated biocatalyst to step (a), wherein said biocatalyst is maintained at a temperature in at least one of steps (a) and (b) or between steps (a) and (b) for a time sufficient to bioconvert at least a portion of the substrate to bioproduct.

The gas phase may be primarily the discontinuous or continuous phase during step (a), and preferably is the continuous phase, i.e., the biocatalyst is suspended in the gas phase. Where the biocatalyst is at least partially suspended, it may, for example, be in the form of a fluidized bed, a riser bed or a loop bed. Where at least partially suspended, the biocatalyst is preferably substantially spherical with a diameter of less than about 5, preferably between about 0.5 to 3, millimeters. Step (a) and the at least one immersion in an aqueous medium may be conducted in the same or different vessels. Where the gas phase is primarily the discontinuous phase, the biocatalyst may be a fixed structure or particles that are touching as in a packed or moving bed.

In preferred aspects, insufficient liquid phase, aqueous medium for maintaining hydration of the biocatalyst, and most preferably no liquid phase aqueous medium (or vapor phase where liquid water condenses on the biocatalyst), is separately introduced for contact with the biocatalyst during step (a). In some more preferred embodiments, at least a portion, preferably essentially all of the biocatalyst, has an essential absence of liquid phase (free liquid phase) on the surface at some time during step (a). For instance, some or all of the biocatalyst being recycled to step (a) after the immersion in aqueous medium may have a free liquid phase on the exterior surface of the biocatalyst, this free liquid phase may be evaporatively or physically removed during step (a). Often, the relative humidity of the gas phase provided for contact with the biocatalyst in step (a) is between about 50 to slightly supersaturated, preferably between about 70 and 100 percent.

Another preferred aspect of this invention pertains to bioconversion processes where the biocatalyst is moved to cycle between vessels, at least one of which provides for contact between feedstock and biocatalyst and another of which provides for bioconversion. In the broad aspects, these bioconversion processes for conducting metabolic processes comprise:

a. contacting fluid feedstock containing substrate with biocatalyst having an interior defined by a solid structure comprised of hydrated, hydrophilic polymer which contains a plurality of interconnected major cavities having a smallest dimension of between about 5 and 100 microns, containing substantially irreversibly retained bioactive material therein in a sorption zone for a time sufficient for at least a portion of the substrate to be sorbed in the biocatalyst and provide a fluid feedstock having a reduced concentration of substrate and loaded biocatalyst containing sorb substrate;

b. withdrawing loaded biocatalyst from the sorption zone;

c. passing said withdrawn biocatalyst to an aqueous medium in a bioreaction zone, said aqueous medium being maintained under conditions suitable for metabolic bioconversion of said substrate;

d. maintaining said biocatalyst and said aqueous medium in the bioreaction zone for a time sufficient to effect bioconversion of at least a portion of the substrate to provide a bioconversion product and biocatalyst having a reduced content of substrate;

e. recovering bioconversion product from said aqueous medium; and f. passing biocatalyst having a reduced content of substrate to the sorption zone.

In a broad aspect, the apparatus of this invention for the bioconversion of substrate contained in a feedstock comprise:

a. an aqueous zone adapted to contain an aqueous medium;

b. a sorption zone adapted to receive biocatalyst and a feedstock containing substrate and adapted to exhaust fluid;

c. a conduit connecting said aqueous zone with said sorption zone, said conduit being adapted to transport biocatalyst from said aqueous zone to said sorption zone, said conduit also containing a liquid-solid separation device adapted to separate aqueous medium from the exterior of biocatalyst; and d. a conduit connecting said sorption zone with said aqueous zone, said conduit being adapted to transport biocatalyst from said sorption zone to said aqueous zone.

Where the apparatus is adapted to receive a feedstock that is gaseous, it is preferred that the conduit connecting said sorption zone with said aqueous zone (d) contains a liquid-solid separation device adapted to separate aqueous medium from the exterior of the biocatalyst.

DETAILED DESCRIPTION

Figure 1:
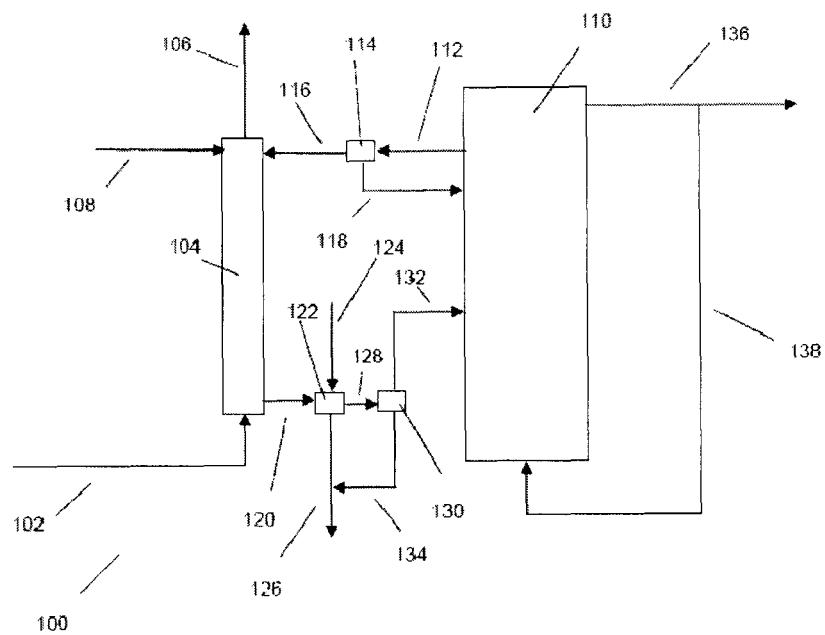
FIG. 1 is a schematic depiction of an apparatus in accordance with this invention that can be used for recovery of substrate from either a gaseous or liquid feedstock and for the conversion of the substrate in a bioreactor.

All patents, published patent applications and articles referenced in this detailed description are hereby incorporated by reference in their entireties.

DEFINITIONS

As used herein, the following terms have the meanings set forth below unless otherwise stated or clear from the context of their use.

The use of the terms "a" and "an" is intended to include one or more of the element described. Lists of exemplary elements are intended to include combinations of one or more of the element described. The term "may" as used herein means that the use of the element is optional and is not intended to provide any implication regarding operability.

Adhering to the solid structure of the biocatalyst means that the bioactive material is located in cavities in the interior of the biocatalyst and is substantially irreversibly retained therein although extraordinary conditions and treatments (i.e., not normal bioconversion conditions for bioconversion using the bioactive material) might be able in some instances to cause the bioactive material to exit the biocatalyst. Adhering includes surface attachment to the polymer forming the walls of the porous matrices as well as where the bioactive material are retained microorganisms that are proximate to a polymeric surface, e.g., within about 10 or 20 microns, but not directly contacting the surface. Adhering thus includes physical and electrostatic adherence. In some instances, the polymer used to make the biocatalyst may become embedded in the extracellular polymeric substance around a cell or even in or on the cell wall of the microorganism.

Bioactive material is one or both of microorganisms and isolated enzymes.

Bioconversion activity is the rate of consumption of substrate per hour per gram of bioactive material. Where an increase or decrease in bioconversion activity is referenced herein, such increase or decrease is ascertained under similar bioconversion conditions including concentration of substrate and product in the aqueous medium. Bioconversion activity to bioproduct is the rate of production of the bioproduct per hour per gram of bioactive material.

Biofilm means an aggregate of microorganisms embedded within an extracellular polymeric substance (EPS) generally composed of polysaccharides, and may contain other components such as one or more of proteins, extracellular DNA and the polymer used to make the biocatalyst. The thickness of a biofilm is determined by the size of the aggregate contained within a continuous EPS structure, but a continuous EPS structure does not include fibrils that may extend between separated biofilms. In some instances, the biofilm extends in a random, three dimensional manner, and the thickness is determined as the maximum, straight line distance between the distal ends. A thin biofilm is a biofilm which does not exceed about 10 microns in any given direction.

Bioproduct means a product of a bioconversion which may be an anabolic product or a catabolic product and includes, but is not limited to, primary and secondary metabolites. Bioproducts include, but are not limited to, sought metabolites, co-products, and by-products, and the metabolites may be final products or intermediate products or a product which has no utility.

A state of essential stasis means that a microorganism population has undergone a substantial cessation of metabolic bioconversion activity but can be revived. The existence of an essential stasis condition can be ascertained by measuring bioconversion activity. The essential stasis condition may be aerobic, anoxic or anaerobic which may or may not be the same as that of normal operating conditions for the microorganism. Where stasis is sought, the temperature is typically in the range of about 0° C. to 25° C., say, 4° C. to 15° C. which may be different from the temperatures used at normal operating conditions.

An exo-network is a community of spaced-apart microorganisms that can be in the form of individual cells or biofilms that are interconnected by extracellular polymeric substance in the form of strands. The spacing between the microorganisms or biofilms in the exo-network is sufficient to enable the passage of nutrients and substrates there between and is often at least about 0.25, say, at least about 0.5, micron and may be as large as 5 or 10 microns or more.

Exterior skin is an exterior layer of polymer on the biocatalyst that is less open than the major channels in the interior structure of the biocatalyst. A biocatalyst may or may not have a skin. Where a skin is present, it may or may not have surface pores. Where no surface pores are present, fluids diffuse through the skin. Where pores are present, they often have an average diameter of between about 1 and 10 microns.

Free liquid phase on the surface of a biocatalyst means the presence of liquid beyond that required for incipient wetness, or filling the pores or capillaries. Often the presence of free liquid results on the surface results in a glistening appearance whereas the absence of free liquid on the surface results in a dull appearance.

Fully hydrated means that a biocatalyst is immersed in water at 25° C. until no further expansion of the superficial volume of the biocatalyst is perceived.

The "Hydration Expansion Volume" (HEV) for a biocatalyst is determined by hydrating the biocatalyst in water at 25° C. until the volume of the biocatalyst has stabilized and measuring the superficial volume of the biocatalyst ($V_w$), removing the biocatalyst from water and removing excess water from the exterior, but without drying, and immersing the biocatalyst in ethanol at 25° C. for a time sufficient that the volume of the biocatalyst has stabilized and then measuring the superficial volume of the biocatalyst ($V_s$).

The HEV in volume percent is calculated as the amount of $[V_w/V_s] \times 100\%$.

To assure dehydration with the ethanol, either a large volume ratio of ethanol to biocatalyst is used or successive immersions of the biocatalyst in fresh ethanol are used. The ethanol is initially dehydrated ethanol.

Irreversibly retained and substantially irreversibly retained mean that the bioactive material is adhering to polymeric structures defining open, porous cavities. Irreversibly retained bioactive material does not include microorganisms located on the exterior surface of a biocatalyst. Bioactive material is irreversibly retained even if the biocatalyst has exterior pores of sufficient size to permit egress of the bioactive material.

Highly hydrophilic polymers are polymers to which water is attracted, i.e., are hydroscopic. Often the polymers exhibit, when cast as a film, a water contact angle of less than about 60°, and sometimes less than about 45°, and in some instances less than about 10°, as measured by the sessile drop method using a 5 microliter drop of pure distilled water.

Highly hydrated means that the volume of the biocatalyst (excluding the volume of the microorganisms) is at least about 90 percent water.

An isolated enzyme is an enzyme removed from a cell and may or may not be in a mixture with other metabolically active or inactive materials.

A matrix is an open, porous, polymeric structure and is an article of manufacture having an interconnected plurality of channels or cavities (herein "major cavities") defined by polymeric structures, said cavities being between about 5 and 100 microns in the smallest dimension (excluding any microorganisms contained therein) wherein fluid can enter and exit the major cavities from and to the exterior of the matrix. The porous matrix may contain larger and smaller channels or cavities than the major cavities, and may contain channels and cavities not open to the exterior of the matrix. The major cavities, that is, open, interconnected regions of between about 5 or 10 to 70 or 100 microns in the smallest dimension (excluding any microorganism contained therein), have nominal major dimensions of less than about 300, preferably less than about 200, microns, and sometimes a smallest dimension of at least about 10 microns. The term open, porous thus refers to the existence of channels or cavities that are interconnected by openings therebetween.

Metabolic conditions include conditions of temperature, pressure, oxygenation, pH, and nutrients (including micronutrients) and additives required or desired for the microorganisms in the biocatalyst. Nutrients and additives include growth promoters, buffers, antibiotics, vitamins, minerals, nitrogen sources, and sulfur sources and carbon sources where not otherwise provided.

A metalate is an oxyanion, hydroxyl or salt of a metal or semiconductor element.

Oxygenated organic product means a product containing one or more oxygenated organic compounds having 2 to 100, and frequently 2 to 50, carbons and at least one moiety selected from the group consisting of hydroxyl, carbonyl, ether and carboxyl.

Permeable means that a component can enter or exit the major cavities from or to the exterior of the biocatalyst.

Quiescent means that the aqueous medium in a biocatalyst is still; however, flows of nutrients and substrates and bioproducts can occur through the aqueous medium via diffusion and capillary flow.

Population of microorganisms refers to the number of microorganisms in a given volume and includes substantially pure cultures and mixed cultures.

A phenotypic change or alternation or phenotypic shift is a change in a microorganism's traits or characteristics from environmental factors and is thus different from a change in the genetic make-up of the microorganism.

Retained solids means that solids are retained in the interior of the biocatalyst. The solids may be retained by any suitable mechanism including, but not limited to, restrained by not being able to pass through pores in the skin of a biocatalyst, by being captured in a biofilm or a polysaccharide structure formed by microorganisms, by being retained in the polymeric structure of the biocatalyst, or by being sterically entangled within the structure of the biocatalyst or the microorganisms.

Smallest dimension means the maximum dimension of the shortest of the maximum dimensions defining the length, width and height of a major cavity. Usually a preponderance of the major cavities in a matrix are substantially width and height symmetrical. Hence the smallest dimension can be approximated by the maximum width of a cavity observed in a two dimensional cross section, e.g., by optical or electronic microscopy.

A solubilized precursor for the polymer is a monomer or prepolymer or the polymer itself that is dissolved or dispersed such that solids cannot be seen by the naked eye and is stable. For instance, a solid can be highly hydrated and be suspended in an aqueous medium even though the solid is not dissolved.

Sorption means any physical or chemical attraction and can be adsorption or absorption and may be relatively weak, e.g., about 10 kilojoules per mole or a chemical interaction with a sorbent. Preferably the sorptive attraction by the sorbent is greater than that between water and the substrate, but not so great that undue energy is required to desorb the substrate. Frequently the sorptive strength is between about 10 and 70, say, 15 and 60, kilojoules per mole. A sorbent is a solid having sorptive capacity for at least one substrate.

A stable population of microorganisms means that the population of microorganisms does not decrease by more than 50 percent nor increase by more than 400 percent.

Substrates are carbon sources, electron donors, electron acceptors and other chemicals that can be metabolized by a microorganism, which chemicals, may or may not provide sustaining value to the microorganisms.

Sugar means carbohydrates having 5 to 12 carbon atoms and includes, but is not limited to, D-glyceraldehyde, L-glyceraldehyde, D-erythrose, L-erythrose, D-threose, L-threose, D-ribose, L-ribose, D-lyxose, L-lyxose, D-allose, L-allose, D-altrose, L-altrose 2-keto-3-deoxy D-gluconate (KDG), D-mannitol, guluronate, mannuronate, mannitol, lyxose, xylitol, D-glucose, L-glucose, D-mannose, L-mannose, D-gluose, L-gluose, D-idose, L-idose, D-galactose, L-galactose, D-xylose, L-xylose, D-arabinose, L-arabinose, D-talose, L-talose, glucuronate, galacturonate, rhamnose, fructooligosaccharide (FOS), galactooligosaccharide (GOS), inulin, mannan oligosaccharide (MOS), oligoalginate, mannuronate, guluronate, alpha-keto acid, or 4-deoxy-L-erythro-hexoselulose uronate (DEHU).

Typical Separation Techniques for chemical products include phase separation for gaseous chemical products, the use of a still, a distillation column, liquid/liquid phase separation, gas stripping, flow-through centrifuge, Karr column for liquid-liquid extraction, mixer-settler, or expanded bed adsorption. Separation and purification steps may proceed by any of a number of approaches combining various methodologies, which may include centrifugation, filtration, reduced pressure evaporation, liquid/liquid phase separation, membranes, distillation, and/or other methodologies recited in this patent application. Principles and details of standard separation and purification steps are known in the art, for example in "Bioseparations Science and Engineering," Roger G. Harrison et al., Oxford University Press (2003), and Membrane Separations in the Recovery of Biofuels and Biochemicals—An Update Review, Stephen A. Leeper, pp. 99-194, in Separation and Purification Technology, Norman N. Li and Joseph M. Calo, Eds., Marcel Dekker (1992).

The wet weight or wet mass of cells is the mass of cells from which free water has been removed, i.e., are at the point of incipient wetness. All references to mass of cells is calculated on the basis of the wet mass of the cells.

References to organic acids herein shall be deemed to include corresponding salts and esters.

References to biocatalyst dimensions and volumes herein are of fully hydrated biocatalyst unless otherwise stated or clear from the context.

Biocatalyst

A. Biocatalyst Overview

The biocatalysts of this invention have a polymeric structure (matrix) defining interconnected major cavities, i.e., are open, porous matrices, in which the bioactive material is retained in the interior of the matrices. Where the bioactive material comprises microorganisms, it is believed that the microorganisms and their communities, inter alia, regulate their population. Also, in conjunction with the sensed nature of the microenvironment in the matrices, it is believed that the microorganisms establish a spatial relationship among the members of the community.

The microorganisms that are retained in the matrices often have the ability to form an exo-network. The quiescent nature of the cavities facilitate forming and then maintaining any formed exo-network. A discernable exo-network is not believed essential to achieving phenotypic alterations in the microorganism population such as population modulation and metabolic shift. Where an exo-network develops, often strands of EPS interconnect proximate microorganisms and connect microorganisms to the surface and form the exo-network. In some instances, the microorganisms form thin biofilms and these thin biofilms are encompassed in the exo-network. The biocatalysts have a substantial absence of biofilms in their interiors that are larger than thin biofilms.

Hence, any biofilms that may ultimately form in the biocatalysts are relatively thin, e.g., up to about 10, and preferably up to about 2 or 5, microns in thickness, and stable in size. Thus, each thin biofilm is often only a few cells and is connected in an exo-network.

Communication among the microorganisms is believed to occur through emitting chemical agents, including, but not limited to, autoinducers, and communication includes communications for community behavior and for signaling. Often, the preparation of the biocatalysts used in the processes of this invention can result in a population of microorganisms being initially located in the interior of the biocatalyst that is substantially that which would exist at the steady-state level. At these densities of microorganisms in the biocatalysts, community communications are facilitated which are believed to commence during the formation of the biocatalysts, and phenotypic shifts occur to enable the metabolic retention and modulate the population of microorganisms.

Another phenotypic alteration occurring in the biocatalysts, which is believed to be a result of this communication, is a metabolic shift, i.e., the metabolic functions of the community towards reproduction are diminished and the sought bioconversion continues. The population of microorganisms in the biocatalyst may tend to have an old average age due to this shift in the metabolic activity. Older microorganisms also tend to provide a more robust and sustainable performance as compared to younger cells as the older cells have adapted to the operating conditions.

Additional benefits of this communication can be an increase in community-level strength or fitness exhibited by the community in warding off adventitious microorganisms and maintaining strain-type uniformity. In some instances, the microorganisms during use of the biocatalyst may undergo natural selection to cause the strain-type in the community to become heartier or provide another benefit for the survival of the community of microorganisms. In some instances, the communication among the microorganisms may permit the population of microorganisms to exhibit multicellularity or multicellular-like behaviors. Thus the population of microorganisms in a biocatalyst of this invention may have microorganisms adapting to different circumstances but yet working in unison for the benefit of the community.

In some instances the porous matrix may provide modulation of the substrate and nutrients to the microorganisms to effect to optimize metabolic pathways involving substrates that are available, and these pathways may or may not be the primarily used pathways where ample substrate and other nutrients are available. Accordingly, microorganisms in the biocatalysts may exhibit enhanced bioactivity for a primarily used pathway or metabolic activity that is normally repressed.

It is also believed that the microenvironments may promote genetic exchange or horizontal gene transfer. Conjugation or bacterial mating may also be facilitated, including the transfer of plasmids and chromosomal elements. Moreover, where microorganisms lyse, strands of DNA and RNA in the microenvironments are more readily accessible to be taken up by microorganisms in these microenvironments. These phenomena can enhance the functional abilities of the microorganisms.

The biocatalysts exhibit an increased tolerance to toxins. In some instances, communications among microorganisms and the exo-network may facilitate the population establishing defenses against toxins. The community response to the presence of toxins has been observed in the biocatalysts of this invention. For instance, the biocatalysts survive the addition of toxins such as ethanol and sodium hypochlorite and the original bioconversion activity is quickly recovered thus indicating the survival of essentially the entire community.

In summary, due to the microenvironments in the biocatalyst, communication among the microorganisms and the phenotypic alterations undergone by the microorganisms, the biocatalysts provide a number of process-related advantages including, but not limited to, no solid debris being generated,
the potential for high densities of bioactive material in a bioreactor,
stable population of microorganisms and bioactivity over extended periods of time,
metabolic shift of microorganisms towards production rather than growth and carbon flow shift,
ability of microorganisms to undergo essential stasis for extended durations,
ability to quickly respond to changes in substrate rate of supply and concentration,
attenuation of diauxie,
enhanced control and modulation of pH and redox balances in the microenvironment of the biocatalyst,
greater tolerance to substrate, bioproduct and contaminants,
ability to bioconvert substrate at ultralow concentrations,
ability to use slower growing and less robust microorganisms and increased resistance to competitiveness,
enhanced microorganism strain purity capabilities,
ability to be subjected to in situ antimicrobial treatment,
ability to quickly start a bioreactor since the density of bioactive material required at full operation is contained in the biocatalyst,
ability to contact biocatalyst with gas phase substrate, and
ease of separation of bioproduct from biocatalyst thereby facilitating continuous operations.

If desired, the biocatalysts, where containing microorganisms, may be treated to enhance the formation of the exo-network, and if desired, thin biofilms, prior to use in the metabolic process. However, performance of the porous matrices is not generally dependent upon the extent of exo-network formation, and often bioconversion activities remain relatively unchanged between the time before the microorganisms have attached to the polymeric structure and the time when extensive exo-network structures have been generated.

B. Physical Description of the Porous Matrices

The biocatalysts of this invention comprise a matrix having open, porous interior structure with bioactive material irreversibly retained in at least the major cavities of the matrix.

The matrices may be a self-supporting structure or may be placed on or in a preformed structure such as a film, fiber or hollow fiber, or shaped article. The preformed structure may be constructed of any suitable material including, but not limited to, metal, ceramic, polymer, glass, wood, composite material, natural fiber, stone, and carbon. Where self-supporting, the matrices are often in the form of sheets, cylinders, plural lobal structures such as trilobal extrudates, hollow fibers, or beads which may be spherical, oblong, or free-form. The matrices, whether self-supporting or placed on or in a preformed structure, preferably have a thickness or axial dimension of less than about 5, preferably less than about 2, say, between about 0.01 to 1, centimeters.

The porous matrices may have an isotropic or, preferably, an anisotropic structure with the exterior portion of the cross section having the densest structure. The major cavities, even if an anisotropic structure exists, may be relatively uniform in size throughout the interior of the matrix or the size of the major cavities, and their frequency, may vary over the cross-section of the biocatalyst.

The biocatalyst of this invention has major cavities, that is, open, interconnected regions of between about 5 or 10 to 70 or 100 microns in the smallest dimension (excluding any microorganisms contained therein). For the purposes of ascertaining dimensions, the dimensions of the microorganisms includes any mass in the exo-network. In many instances, the major cavities have nominal major dimensions of less than about 300, preferably less than about 200, microns, and sometimes a smallest dimension of at least about 10 microns. Often the biocatalyst contains smaller channels and cavities which are in open communication with the major cavities. Frequently the smaller channels have a maximum cross-sectional diameter of between about 0.5 to 20, e.g., 1 to 5 or 10, microns. The cumulative volume of major cavities, excluding the volume occupied by microorganisms and mass associated with the microorganisms, to the volume of the biocatalyst is generally in the range of about 40 or 50 to 70 or 99, volume percent. In many instances, the major cavities constitute less than about 70 percent of the volume of the fully catalyst with the remainder constituting the smaller channels and pores. The volume fraction of the biocatalyst that constitute the major cavities can be estimated from its cross-section. The cross section may be observed via any suitable microscopic technique, e.g., scanning electron microscopy and high powered optical microscopy. The total pore volume for the matrices can be estimated from the volumetric measurement of the matrices and the amount and density of polymer, and any other solids used to make the matrices.

The biocatalyst is characterized by having high internal surface areas, often in excess of at least about 1 and sometimes at least about 10, square meter per gram. In some instances, the volume of water that can be held by a fully hydrated biocatalyst (excluding the volume of the microorganisms) is in the range of 90 to 99 or more, percent. Preferably the biocatalyst exhibits a Hydration Expansion Volume (HEV) of at least about 1000, frequently at least about 5000, preferably at least about 20,000, and sometimes between 50,000 and 200,000, percent.

Usually the type of polymer selected and the void volume percent of the matrices are such that the matrices have adequate strength to enable handling, storage and use in a bioconversion process.

The porous matrices may or may not have an exterior skin. Preferably the matrices have an exterior skin to assist in modulating the influx and efflux of components to and from the interior channels of the porous matrix. Also, since the skin is highly hydrophilic, and additional benefit is obtained as contaminating or adventitious microorganisms have difficulties in establishing a strong biofilm on the exterior of the biocatalyst. These contaminating microorganisms are often subject to removal under even low physical forces such as by the flow of fluid around the biocatalysts. Thus, the fouling of the biocatalyst can be substantially eliminated or mitigated by washing or by fluid flows during use.

Where present, the skin typically has pores of an average diameter of between about 1 and 10, preferably 2 to 7, microns in average diameter. The pores may comprise about 1 to 30, say, 2 to 20, percent of the external surface area. The external skin, in addition to providing a barrier to entry of adventitious microorganisms into the interior of the biocatalyst, is preferably relatively smooth to reduce the adhesion of microorganisms to the external side of the skin through physical forces such as fluid flow and contact with other solid surfaces. Often, the skin is substantially devoid of anomalies, other than pores, greater than about 2 or 3 microns. Where a skin is present, its thickness is usually less than about 50, say, between about 1 and 25, microns. It should be understood that the thickness of the skin can be difficult to discern where the porous matrix has an anisotropic structure with the densest structure being at the exterior of the matrix.

A high concentration of isolated enzyme and or density of microorganisms can exist at steady-state operation within the biocatalysts. The combination of the flow channels and the high permeability of the polymeric structure defining the channels enable viable microorganism population throughout the matrix, albeit with a plurality of unique microenvironments and nano-environments. In some instances, when the bioactive material comprises microorganisms, the cell density based upon the volume of the matrices is preferably at least about 100 grams per liter, preferably at least about 200, and often between about 250 and 750, grams per liter.

Polysaccharide-Containing Biocatalysts

By incorporating polysaccharide in the interior of the biocatalyst, the viability of the microorganism population can be maintained. Typically polysaccharides are not usable by most microorganisms. Often, the polysaccharide is provided in an amount of at least about 0.1, say, at least about 0.2 to 100, gram per gram of cells retained in the biocatalyst, and sometimes the biocatalyst contains between 25 and 500 grams of polysaccharide per liter of volume of fully hydrated biocatalyst. The polysaccharide particles used in preparing the biocatalysts preferably have a major dimension of less than about 50, preferably less than about 20, often between about 0.1 to 5, microns. The solid polysaccharide particles are preferably granular and often have an aspect ratio of minimum cross-sectional dimension to maximum cross sectional dimension of between about 1:10 to 1:1, say 1:2 to 1:1.

Due to the ability of the polysaccharide to maintain the viability of the microorganisms in the biocatalyst, the storage, handling and processes for use of the biocatalyst can be facilitated. For instance, the biocatalysts can be used in bioconversion processes which are operated in a carbon deficient manner. In metabolic processes where carbon source is added to maintain the microorganisms and not used in the sought bioconversion of substrate to bioproduct, such as in the catabolysis of nitrate, nitrite, and perchlorate anions and the metabolic reduction of metalates, the polysaccharide may serve as the sole source of carbon and thereby eliminate the necessity of adding carbon source, or it may reduce the amount of carbon source added, i.e., permit carbon deficient operation. An advantage is that the bioprocesses can be operated such that the effluent has essentially no COD. The biocatalysts also have enhanced abilities to tolerate disruptions in substrate presence and be able to quickly regain bioconversion activity. Also, the biocatalysts can be remotely manufactured and shipped to the location of use without undue deleterious effect on the bioconversion activity of the biocatalyst. The biocatalysts may be able enter a state of essential stasis for extended durations of time in the absence of supplying substrate and other nutrients to the microbial composites even where excursions in the desired storage conditions such as temperature occur. The bioactivity can be quickly regained in a bioreactor even after extended episodic occurrences of shutdown, feedstock disruption, or feedstock variability. The biocatalysts can be packaged and shipped in sealed barrels, tanks, and the like. The polysaccharide may be from any suitable source including, but not limited to, cellulosic polysaccharides or starches. Polysaccharides are carbohydrates characterized by repeating units linked together by glycosidic bonds and are substantially insoluble in water. Polysaccharides may be homopolysaccharides or heteropolysaccharides and typically have a degree of polymerization of between about 200 and 15,000 or more, preferably between about 200 and 5000. The preferred polysaccharides are those in which about 10, more preferably, at least about 20, percent of the repeating units are amylose (D-glucose units). Most preferably the polysaccharide has at least about 20, more preferably, at least about 30, percent of the repeating units being amylose. The polysaccharides may or may not be functionalized, e.g., with acetate, sulfate, phosphate, pyruvyl cyclic acetal, and the like, but such functionalization should not render the polysaccharide water soluble at temperatures below about 50° C. A preferred class of polysaccharides is starches.

Sources of polysaccharides include naturally occurring and synthetic (e.g., polydextrose) polysaccharides. Various plant based materials providing polysaccharides include but are not limited to woody plant materials providing cellulose and hemicellulose, and wheat, barley, potato, sweet potato, tapioca, corn, maize, cassava, milo, rye and brans typically providing starches.

Solid Sorbent-Containing Biocatalysts

The biocatalysts may contain a solid sorbent. The solid sorbent may be the hydrophilic polymer forming the structure or may be a particulate, i.e., a distinct solid structure regardless of shape) contained in the solid structure. The sorbent may be any suitable solid sorbent for the substrate or nutrients or other chemical influencing the sought metabolic activity such as, but not limited to, co-metabolites, inducers, and promoters or for components that may be adverse to the microorganisms such as, and not in limitation, toxins, phages, bioproducts and by-products. The solid sorbent is typically an adsorbent where the sorption occurs on the surface of the sorbent. The particulate solid sorbents are preferably nano materials having a major dimension less than about 5 microns, preferably, between about 5 nanometers to 3 microns. Where the solid sorbent is composed of polymer, the solid structure may be essentially entirely composed of the polymer or may be a block copolymer or polymeric mixture constituting between about 5 and 90 mass percent of the solid structure (excluding water). Where the solid sorbent is a separate particulate in the biocatalyst, the biocatalyst may comprise between about 5 to 90 mass percent of the mass of the biocatalyst (excluding water and microorganisms but including both the hydrophilic polymer and the particulates). More than one solid sorbent may be used in a biocatalyst. Preferably the solid sorbent is relatively uniformly dispersed throughout the interior of the biocatalyst although the solid sorbent may have a varying distribution within the biocatalyst. Where the distribution varies, the regions with the higher concentration of solid sorbent often are found toward the surface of the biocatalyst.

Where a particulate sorbent is used, the sorbent comprises an organic or inorganic material having the sought sorptive capacity. Examples of solid sorbents include, without limitation, polymeric materials, especially with polar moieties, carbon (including but not limited to activated carbon), silica (including but not limited to fumed silica), silicates, clays, molecular sieves, and the like. The molecular sieves include, but are not limited to zeolites and synthetic crystalline structures containing oxides and phosphates of one or more of silicon, aluminum, titanium, copper, cobalt, vanadium, titanium, chromium, iron, nickel, and the like. The sorptive properties may comprise one or more of physical or chemical or quasi-chemical sorption on the surface of the solid sorbent. Thus, surface area and structure may influence the sorptive properties of some solid sorbents. Frequently the solid sorbents are porous and thus provide high surface area and physical sorptive capabilities. Often the pores in the solid sorbents are in the range of about 0.3 to 2 nanometers in effective diameter.

The solid sorbent may be incorporated into the polymeric structure in any convenient manner, preferably during the preparation of the biocatalyst.

Phosphorescent Biocatalysts

Another preferred aspect of the invention pertains to biocatalysts containing phosphorescent material and photosynthetic microorganisms, i.e., microorganisms that uses light energy in a metabolic process. Preferably the microorganism is an algae, most preferably a microalgae, or cyanobacteria.

The bioactivity of photosynthetic microorganisms can be enhanced to produce expressed bioproduct using broad-based light source such as sunlight. In accordance with the invention, the photosynthetic microorganisms are irreversibly retained in biocatalysts in which the interior of the biocatalyst contains phosphorescent material capable of shifting UV light to light having a wavelength of between about 400 and 800, preferably between about 450 and 650, nm and is capable of exhibiting persistence, with the emission of the light often lasting for at least about 5 seconds. A phosphorescent material is a material that has the ability to be excited by electromagnetic radiation into an excited state, but the stored energy is released gradually. Emissions from phosphorescent materials have persistence, that is, emissions from such materials can last for seconds, minutes or even hours after the excitation source is removed. A luminescent material is a material capable of emitting electromagnetic radiation after being excited into an excited state. Persistence is the time it takes, after discontinuing irradiation, for photoluminescent emissions emanating from a photoluminescent object to decrease to the threshold detectability.

The persistence of the radiation enables the microorganisms to be cycled in and out of a region of the culture liquid exposed to the light source and still be productive. With longer persistence durations, the photosynthetic microorganisms can continue photo-bioconversion in the absence of or reduction in light intensity. The ability of the biocatalysts to maintain photosynthetic activity over extended periods of time, often at least about 30 days, and in some instances for at least one year, the cost of the phosphorescent materials is well offset by the increased production, reduced footprint of the bioreactor, and facilitated bioproduct recovery.

The biocatalyst, being highly hydrated is a significant distributor of light radiation to photosynthetic microorganisms retained in the interior of the biocatalyst and also serves to protect the microorganism from photorespiration. The solid debris in the culture liquid (an aqueous solution comprising nutrients for metabolic processes) can be materially reduced, if not essentially eliminated, due to the microorganisms being irreversibly retained in the biocatalyst. Thus the turbidity is reduced and a given light intensity can thus be found at a greater depth in the culture liquid. These advantages provided by the biocatalysts of this invention can be realized in any photosynthetic process regardless of whether or not a phosphorescent material is used.

Examples of phosphorescent materials include, but are not limited to, phosphorescent materials are metal sulfide phosphors such as ZnCdS:Cu:Al, ZnCdS:Ag:Al, ZnS:Ag: Al, ZnS:Cu:Al as described in U.S. Pat. No. 3,595,804 and metal sulfides that are co-activated with rare earth elements such as those describe in U.S. Pat. No. 3,957,678. Phosphors that are higher in luminous intensity and longer in luminous persistence than the metal sulfide pigments include compositions comprising a host material that is generally an alkaline earth aluminate, or an alkaline earth silicate. The host materials generally comprise Europium as an activator and often comprise one or more co-activators such as elements of the Lanthanide series (e.g. lanthanum, cerium, praseodymium, neodymium, samarium, gadolinium, terbium, dysprosium, holmium, erbium, thulium, ytterbium, and lutetium), tin, manganese, yttrium, or bismuth. Examples of such phosphors are described in U.S. Pat. No. 5,424,006.

High emission intensity and persistence phosphorescent materials can be alkaline earth aluminate oxides having the formula $MO_mAl_2O_3:Eu^{2+}, R^{3+}$ wherein m is a number ranging from 1.6 to about 2.2, M is an alkaline earth metal (strontium, calcium or barium), $Eu^{2+}$ is an activator, and R is one or more trivalent rare earth materials of the lanthanide series (e.g. lanthanum, cerium, praseodymium, neodymium, samarium, gadolinium, terbium, dysprosium, holmium, erbium, thulium, ytterbium, lutetium), yttrium or bismuth co-activators. Examples of such phosphors are described in U.S. Pat. No. 6,117,362. Phosphorescent materials also include alkaline earth aluminate oxides having the formula $M_kAl_2O_4:2xEu^{2+}, 2yR^{3+}$ wherein k=1−2x−2y, x is a number ranging from about 0.0001 to about 0.05, y is a number ranging from about x to 3x, M is an alkaline earth metal (strontium, calcium or barium), $Eu^{2+}$ is an activator, and R is one or more trivalent rare earth materials (e.g. lanthanum, cerium, praseodymium, neodymium, samarium, gadolinium, terbium, dysprosium, holmium, erbium, thulium, ytterbium, lutetium), yttrium or bismuth co-activators. See U.S. Pat. No. 6,267,911B1.

Phosphorescent materials also include those in which a portion of the $Al^{3+}$ in the host matrix is replaced with divalent ions such as $Mg^{2+}$ or $Zn^{2+}$ and those in which the alkaline earth metal ion ($M^{2+}$) is replaced with a monovalent alkali metal ion such as $Li^+$, $Na^+$, $K^+$, $Cs^+$ or $Rb^+$ such as described in U.S. Pat. Nos. 6,117,362 and 6,267,911B1.

High intensity and high persistence silicates have been disclosed in U.S. Pat. No. 5,839,718, such as Sr.BaO.Mg-.MO.SiGe:Eu:Ln wherein M is beryllium, zinc or cadmium and Ln is chosen from the group consisting of the rare earth materials, the group 3A elements, scandium, titanium, vanadium, chromium, manganese, yttrium, zirconium, niobium, molybdenum, hafnium, tantalum, tungsten, indium, thallium, phosphorous, arsenic, antimony, bismuth, tin, and lead. Particularly useful are dysprosium, neodymium, thulium, tin, indium, and bismuth. X in these compounds is at least one halide atom.

Other phosphorescent materials include alkaline earth aluminates of the formula $MO.Al_2O_3.B_2O_3:R$ wherein M is a combination of more than one alkaline earth metal (strontium, calcium or barium or combinations thereof) and R is a combination of $Eu^{2+}$ activator, and at least one trivalent rare earth material co-activator, (e.g. lanthanum, cerium, praseodymium, neodymium, samarium, gadolinium, terbium, dysprosium, holmium, erbium, thulium, ytterbium, lutetium), bismuth or manganese. Examples of such phosphors can be found in U.S. Pat. No. 5,885,483. Alkaline earth aluminates of the type $MAl_2O_4$, which are described in U.S. Pat. No. 5,424,006, may also find application as may phosphorescent materials comprising a donor system and an acceptor system such as described in U.S. Pat. No. 6,953, 536 B2.

As can be appreciated, many other phosphors can find application. See, for instance, Yen and Weber, Inorganic Phosphors: Compositions, Preparation and Optical Properties, CRC Press, 2004.

The phosphorescent material may be a discrete particle or may be a particle having a coating to facilitate incorporation and retention in the polymer forming the matrix. The particles may be of any suitable shape. Generally the maximum dimension of the of the particles is less than about 1 millimeter, preferably less than about 0.1 millimeter. The particles may be nanoparticles.

The persistence time exhibited by the phosphorescent materials can range from a short duration, e.g., about 5 to 10 seconds, to as much as 10 or 20 hours or more and will be dependent upon the phosphorescent material used. Preferred phosphorescent materials exhibit a persistence of at least about one minute. The intensity of the emitted radiation from the polymer of the matrices will, in part, depend upon the concentration of the phosphorescent material in the polymer and the nature of the phosphorescent material. Typically the phosphorescent material is provided in an amount of at least about 0.1, say, between 0.2 and 5 or 10, mass percent of the polymer (non-hydrated) in the biocatalyst. One or more phosphorescent materials may be used in the biocatalyst. Where more than one phosphorescent material are used, the combination may be selected to provide one or more of wave shifting from different light wavelengths contained in the band width of the radiation source and providing differing persistence times. In preferred embodiments the phosphorescent materials are in the form of nanoparticles, e.g., having a major dimension of between about 10 nm and 10 μm. In some instances, it may be desired to coat the phosphorescent materials with a compatibilizing agent to facilitate incorporation of the phosphorescent material within the polymer. Compatibilizing agents include, but are not limited to, molecules having one or more of hydroxyl, thiol, silyl, carboxyl, or phosphoryl groups.

C. Methods for Making Biocatalysts

The components, including bioactive materials, used to make the biocatalysts and the process conditions used for the preparation of the biocatalysts are not critical to the broad aspects of this invention and may vary widely as is well understood in the art once understanding the principles described above. In any event, the components and process conditions for making the biocatalysts with the irreversibly, metabolically retained microorganisms should not adversely affect the microorganisms.

The biocatalysts may be prepared from a liquid medium containing the bioactive material and solubilized precursor for the hydrophilic polymer which may be one or more of a polymerizable or solidifiable component or a solid that is fusible or bondable to form the matrix. Aqueous media are most often used due to the compatibility of most microorganisms and enzymes with water. However, with bioactive materials that tolerate other liquids, such liquids can be used to make all or a portion of the liquid medium. Examples of such other liquids include, but are not limited to liquid hydrocarbons, peroxygenated liquids, liquid carboxy-containing compounds, and the like. Mixed liquid media can also be used to prepare the biocatalyst. The mixed media may comprise miscible or immiscible liquid phases. For instance, the bioactive material may be suspended in a dispersed, aqueous phase and the polymerizable or solidifiable component may be contained in a continuous solvent phase.

The liquid medium used to prepare the biocatalyst may contain more than one type of microorganism, especially where the microorganisms do not significantly compete for the same substrate, and may contain one or more isolated enzymes or functional additives such as polysaccharide, solid sorbent and phosphorescent materials, as described above. Preferably, the biocatalysts contain a single type of microorganism. The concentration of the microorganisms in the liquid medium used to make the biocatalysts should at least be about 60 grams per liter. As discussed above, the concentration of microorganisms should preferably approximate the sought density of microorganisms in the biocatalyst. The relative amounts of microorganism and polymeric material in forming the biocatalyst can vary widely. The growth of the population of microorganisms post formation of the biocatalyst is contemplated as well as the potential for damage to some of the population of microorganisms during the biocatalyst-forming process. Nevertheless, higher microorganism concentrations are generally preferred, e.g., at least about 100 grams per liter, preferably at least about 200, and often between about 250 and 750, grams per liter of the liquid medium used to make the biocatalysts.

Any suitable process may be used to solidify or polymerize the polymeric material or to adhere or fuse particles to form the open, porous polymeric matrix with bioactive material irreversibly retained therein. The conditions of suitable processes should not unduly adversely affect the bioactive material. As bioactive materials differ in tolerance to temperatures, pressures and the presence of other chemicals, some matrix-forming processes may be more advantageous for one type of bioactive material than for another type of bioactive material.

Preferably the polymeric matrix is formed from solidification of a high molecular weight material, by polymerization or by cross-linking of prepolymer in manner that a population of microorganisms is provided in the interior of the biocatalyst as it is being formed. Exemplary processes include solution polymerization, slurry polymerization (characterized by having two or more initial phases), and solidification by cooling or removal of solvent.

The biocatalysts may be formed in situ in the liquid medium by subjecting the medium to solidification conditions (such as cooling or evaporation) or adding a component to cause a polymerization or cross-linking or agglomeration of solids to occur to form a solid structure such as a catalyst, cross-linking agent or coagulating agent. Alternatively, the liquid medium may be extruded into a solution containing a solidification agent such as a catalyst, cross-linking or coagulating agent or coated onto a substrate and then the composite subjected to conditions to form the solid biocatalyst.

Polymeric materials used to make the biocatalysts may have an organic or inorganic backbone but have sufficient hydrophilic moieties to provide a highly hydrophilic polymer which when incorporated into the matrices exhibits sufficient water sorption properties to provide the sought Hydration Expansion Volume of the biocatalyst. Polymeric materials are also intended to include high molecular weight substances such as waxes (whether or not prepared by a polymerization process), oligomers and the like so long as they form biocatalysts that remain solid under the conditions of the bioconversion process intended for their use and have sufficient hydrophilic properties that the Hydration Expansion Volume can be achieved. As stated above, it is not essential that polymeric materials become cross-linked or further polymerized in forming the polymeric matrix.

Examples of polymeric materials include homopolymers and copolymers which may or may not be cross-linked and include condensation and addition polymers that provide high hydrophilicity and enable the Hydration Expansion Volumes to be obtained. The polymer may be a homopolymer or a copolymer, say, of a hydrophilic moiety and a more hydrophobic moiety. The molecular weight and molecular weight distribution are preferably selected to provide the combination of hydrophilicity and strength as is known in the art. The polymers may be functionalized with hydrophilic moieties to enhance hydrophilicity. Examples of hydrophilic moieties include, but are not limited to hydroxyl, alkoxyl, acyl, carboxyl, amido, and oxyanions of one or more of titanium, molybdenum, phosphorus, sulfur and nitrogen such as phosphates, phosphonates, sulfates, sulfonates, and nitrates, and the hydrophilic moieties may be further substituted with hydrophilic moieties such as hydroxyalkoxides, acetylacetonate, and the like. Typically the polymers contain carbonyl and hydroxyl groups, especially at some adjacent hydrophilic moieties such as glycol moieties. In some instances, the backbone of the polymer contains ether oxygens to enhance hydrophilicity. In some instances, the atomic ratio of oxygen to carbon in the polymer is between about 0.3:1 to 5:1.

Polymers which may find use in forming the matrices include functionalized or non-functionalized polyacrylamides, polyvinyl alcohols, polyetherketones, polyurethanes, polycarbonates, polysulfones, polysulfides, polysilicones, olefinic polymers such as polyethylene, polypropylene, polybutadiene, rubbers, and polystyrene, nylons, polythyloxazyoline, polyethylene glycol, polysaccharides such as sodium alginate, carageenan, agar, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan, and proteins such as gelatin, collagen and albumin, which may be polymers, prepolymers or oligomers, and polymers and copolymers from the following monomers, oligomers and prepolymers:

monomethacrylates such as polyethylene glycol monomethacrylate, polypropylene glycol monomethacrylate, polypropylene glycol monomethacrylate, methoxydiethylene glycol methacrylate, methoxypolyethylene glycol methacrylate, methacryloyloxyethyl hydrogen phthalate, methacryloyloxyethyl hydrogen succinate, 3-chloro-2-hydroxypropyl methacrylate, stearyl methacrylate, 2-hydroxy methacrylate, and ethyl methacrylate;

monoacrylates such as 2-hydroxyethyl acrylate, 2-hydroxypropyl acrylate, isobutyl acrylate, t-butyl acrylate, isooctyl acrylate, lauryl acrylate, stearyl acrylate, isobornyl acrylate, cyclohexyl acrylate, methoxytriethylene glycol acrylate, 2-ethoxyethyl acrylate, tetrahydrofurfuryl acrylate, phenoxyethyl acrylate, nonylphenoxypolyethylene glycol acrylate, nonylphenoxypolypropylene glycol acrylate, silicon-modified acrylate, polypropylene glycol monoacrylate, phenoxyethyl acrylate, phenoxydiethylene glycol acrylate, phenoxypolyethylene glycol acrylate, methoxypolyethylene glycol acrylate, acryloyloxyethyl hydrogen succinate, and lauryl acrylate;

dimethacrylates such as 1,3-butylene glycol dimethacrylate, 1,4-butanediol dimethacrylate, ethylene glycol dimethacrylate, diethylene glycol dimethacrylate, triethylene glycol dimethacrylate, polyethylene glycol dimethacrylate, butylene glycol dimethacrylate, hexanediol dimethacrylate, neopentyl glycol dimethacrylate, polyprene glycol dimethacrylate, 2-hydroxy-1,3-dimethacryloxypropane, 2,2-bis-4-methacryloxyethoxyphenylpropane, 3,2-bis-4-methacryloxydiethoxyphenylpropane, and 2,2-bis-4-methacryloxypolyethoxyphenylpropane;

diacrylates such as ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxyethoxyphenylpropane, 2-hydroxy-1-acryloxy-3-methacryloxypropane; trimethacrylates such as trimethylolpropane trimethacrylate; triacrylates such as trimethylolpropane triacrylate, pentaerythritol triacrylate, trimethylolpropane EO-added triacrylate, glycerol PO-added triacrylate, and ethoxylated trimethylolpropane triacrylate; tetraacrylates such as pentaerythritol tetraacrylate, ethoxylated pentaerythritol tetraacrylate, propoxylated pentaerythritol tetraacrylate, and ditrimethylolpropane tetraacrylate;

urethane acrylates such as urethane acrylate, urethane dimethyl acrylate, and urethane trimethyl acrylate;

amino-containing moieties such as 2-aminoethyl acrylate, 2-aminoethyl methacrylate, aminoethyl methacrylate, dimethyl aminoethyl methacrylate, monomethyl aminoethyl methacrylate, t-butylaminoethylmethacrylate, p-aminostyrene, o-aminostyrene, 2-amino-4-vinyltoluene, dimethylaminoethyl acrylate, diethylaminoethyl acrylate, piperidinoethyl ethyl acrylate, piperidinoethyl methacrylate, morpholinoethyl acrylate, morpholinoethyl methacrylate, 2-vinyl pyridine, 3-vinyl pyridine, 2-ethyl-5-vinyl pyridine, dimethylaminopropylethyl acrylate, dimethylaminopropylethyl methacrylate, 2-vinyl pyrrolidone, 3-vinyl pyrrolidone, dimethylaminoethyl vinyl ether, dimethylaminoethyl vinyl sulfide, diethylaminoethyl vinyl ether, 2-pyrrolidinoethyl acrylate, 2-pyrrolidinoethyl methacrylate, and other monomers such as acrylamide, acrylic acid, and dimethylacrylamide.

Not all the above listed polymers will be useful by themselves, but may be required to be functionalized or used to form a co-polymer with a highly hydrophilic polymer.

Cross linking agents, accelerators, polymerization catalysts, and other polymerization additives may be employed such as triethanolamine, triethylamine, ethanolamine, N-methyl diethanolamine, N,N-dimethyl benzylamine, dibenzyl amino, N-benzyl ethanolamine, N-isopropyl benzylamino, tetramethyl ethylenediamine, potassium persulfate, tetramethyl ethylenediamine, lysine, ornithine, histidine, arginine, N-vinyl pyrrolidinone, 2-vinyl pyridine, 1-vinyl imidazole, 9-vinyl carbazone, acrylic acid, and 2-allyl-2-methyl-1,3-cyclopentane dione. For polyvinyl alcohol polymers and copolymers, boric acid and phosphoric acid may be used in the preparation of polymeric matrices. As stated above, the amount of cross-linking agent may need to be limited to assure that the matrices retain high hydrophilicity and the ability to have a high Hydration Expansion Volume. The selection of the polymer and cross-linking agents and other additives to make porous matrices having the physical properties set forth above is within the level of the artisan in the art of water soluble and highly hydrophilic polymer synthesis.

The biocatalysts may be formed in the presence of other additives which may serve to enhance structural integrity or provide a beneficial activity for the microorganism such as attracting or sequestering components, providing nutrients, and the like. Additives can also be used to provide, for instance, a suitable density to be suspended in the aqueous medium rather than tending to float or sink in the broth. Typical additives include, but are not limited to, starch, glycogen, cellulose, lignin, chitin, collagen, keratin, clay, alumina, aluminosilicates, silica, aluminum phosphate, diatomaceous earth, carbon, polymer, polysaccharide and the like. These additives can be in the form of solids when the polymeric matrices are formed, and if so, are often in the range of about 0.01 to 100 microns in major dimension.

If desired, where the biocatalyst contains microorganisms, they may be subjected to stress as is known in the art. Stress may be one or more of starvation, chemical or physical conditions. Chemical stresses include toxins, antimicrobial agents, and inhibitory concentrations of compounds. Physical stresses include light intensity, UV light, temperature, mechanical agitation, pressure or compression, and desiccation or osmotic pressure. The stress may produce regulated biological reactions that protect the microorganisms from shock and the stress may allow the hardier microorganisms to survive while the weaker cells die.

Bioactive Material

The bioactive material is one or more of isolated enzymes and microorganisms. In another aspect, the biocatalysts can contain, in addition to the microorganisms, one or more extracellular enzymes in the interior of the biocatalyst to cause a catalytic change to a component which may be substrate or other nutrients, or a bioproduct or by-product or co-product of the microorganisms, or may be a toxin, phage or the like.

Examples of enzymes include, but are not limited to, one or more of oxidoreductases, transferases, hydrolases, lyases, isomerases, and ligases. The enzymes may cause one or more metabolic conversions. For instance, an enzyme may metabolize a component in the feed such that it can be bioconverted, or more easily be bioconverted, by the microorganisms in the biocatalyst. An enzyme may be used to metabolize a metabolite of the microorganism either to provide a sought bioproduct. An enzyme may be used to metabolize a component in the feed or a co-metabolite from the microorganism that may be adverse to the microorganism into a metabolite that is less adverse to the microorganism. If desired, two or more different enzymes can be used to effect a series of metabolic conversions on a component in the feed or a metabolite from the microorganism.

Representative enzymes include, without limitation: cellulase, cellobiohydrolase (e.g., CBHI, CBHII), alcohol dehydrogenase (A, B, and C), acetaldehyde dehydrogenase, amylase, alpha amylase, glucoamylase, beta glucanase, beta glucosidase, invertase, endoglucanase (e.g., EGI, EGII, EGIII), lactase, hemicellulase, pectinase, hydrogenase, pullulanase, phytase, a hydrolase, a lipase, polysaccharase, ligninase, Accellerase® 1000, Accellerase® 1500, Accellerase® DUET, Accellerase® TRIO, or Cellic CTec2 enzymes, phosphoglucose isomerase, inositol-1-phosphate synthase, inositol monophosphatase, myo-inositol dehydrogenase, myo-inosose-2-dehydratase, inositol 2-dehydrogenase, deoxy-D-gluconate isomerase, kinase, 5-dehydro-2-deoxygluconokinase, deoxyphophogluconate aldolase, 3-hydroxy acid dehydrogenase, isomerase, topoisomerase, dehydratase, monosaccharide dehydrogenase, aldolase, phosphatase, a protease, DNase, alginate lyase, laminarinase, endoglucanase, L-butanediol dehydrogenase, acetoin reductase, 3-hydroxyacyl-CoA dehydrogenase, or cis-aconitate decarboxylase. The enzymes include those described by Heinzelman et al. (2009) *PNAS* 106: 5610-5615, herein incorporated by reference in its entirety.

The enzymes may be bound to the precursor for the hydrophilic polymer of the biocatalyst prior to the formation of the biocatalyst or may be introduced during the preparation of the biocatalyst, e.g., by addition to the liquid medium for forming the biocatalyst. There are many methods that would be known to one of skill in the art for providing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process. Various methods are described in Methods in Enzymology, Immobilized Enzymes and Cells, Part C. 1987. Academic Press. Edited by S. P. Colowick and N. O. Kaplan. Volume 136; Immobilization of Enzymes and Cells. 1997. Humana Press. Edited by G. F. Bickerstaff. Series: Methods in Biotechnology, Edited by J. M. Walker; DiCosimo, R., McAuliffe, J., Poulose, A. J. Bohlmann, G. 2012. Industrial use of immobilized enzymes. Chem. Soc. Rev.; and Immobilized Enzymes: Methods and Applications. Wilhelm Tischer and Frank Wedekind, Topics in Current Chemistry, Vol. 200. Page 95-126.

Typically extracellular enzymes bond or adhere to solid surfaces, such as the hydrophilic polymer, solid additives, cell walls and extracellular polymeric substance. Hence, the enzymes can be substantially irreversibly retained in the interior of the biocatalyst. Due to the structure of the biocatalysts of this invention, the microorganisms and the enzymes can be in close proximity and thus effective, cooperative bioconversions can be obtained. The association of the enzymes with the interior surfaces of the biocatalyst typically increases the resistance of the enzyme or enzymes to denaturation due to changes in temperature, pH, or other factors related to thermal or operational stability of the enzymes. Also, by being retained in the biocatalyst, the use of the enzyme in a bioreactor is facilitated and undesirable post-reactions can be mitigated.

Where the bioactive material comprises microorganisms, the microorganisms may be unicellular or may be multicellular that behaves as a single cell microorganism such as filamentous growth microorganisms and budding growth microorganisms. Often the cells of multicellular microorganisms have the capability to exist singularly. The microorganisms can be of any type, including, but not limited to, those microorganisms that are aerobes, anaerobes, facultative anaerobes, heterotrophs, autotrophs, photoautotrophs, photoheterotrophs, chemoautotrophs, and/or chemoheterotrophs. The cellular activity, including cell growth can be aerobic, microaerophilic, or anaerobic. The cells can be in any phase of growth, including lag (or conduction), exponential, transition, stationary, death, dormant, vegetative, sporulating, etc. The one or more microorganisms be a psychrophile (optimal growth at −10° C. to 25° C.), a mesophile (optimal growth at 20-50° C.), a thermophile (optimal growth 45° C. to 80° C.), or a hyperthermophile (optimal growth at 80° C. to 100° C.). The one or more microorganisms can be a gram-negative or gram-positive bacterium. A bacterium can be a cocci (spherical), bacilli (rod-like), or spirilla (spiral-shaped; e.g., vibrios or comma bacteria). The microorganisms can be phenotypically and genotypically diverse.

The microorganisms can be a wild-type (naturally occurring) microorganism or a recombinant (including, but not limited to genetically engineered microorganisms) microorganism. A recombinant microorganism can comprise one or more heterologous nucleic acid sequences (e.g., genes). One or more genes can be introduced into a microorganism used in the methods, compositions, or kits described herein, e.g., by homologous recombination. One or more genes can be introduction into a microorganism with, e.g., a vector. The one or more microorganisms can comprise one or more vectors. A vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain a means for self-replication. The vector can, when introduced into a host cell, integrate into the genome of the host cell and replicate together with the one or more chromosomes into which it has been integrated. Such a vector can comprise specific sequences that can allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants. Means of genetically manipulating organisms are described, e.g., Current Protocols in Molecular Biology, last updated Jul. 25, 2011, Wiley, Print ISSN: 1934-3639. In some embodiments, one or more genes involved in byproduct formation are deleted in a microorganism. In some embodiments, one or more genes involved in byproduct formation are not deleted. Nucleic acid introduced into a microorganism can be codon-optimized for the microorganism. A gene can be modified (e.g., mutated) to increase the activity of the resulting gene product (e.g., enzyme).

The selected microorganism to be used in a biocatalyst can be targeted to the sought activity. The biocatalysts thus often contain substantially pure strain types of microorganisms and, because of the targeting, enable high bioactivity to be achieved and provide a stable population of the microorganism in the biocatalyst.

Representative microorganisms for making biocatalysts of this invention include, without limitation, those set forth in United States published patent application nos. 2011/0072714, especially paragraph 0122; 2010/0279354, especially paragraphs 0083 through 0089; 2011/0185017, especially paragraph 0046; 2009/0155873; especially paragraph 0093; and 20060063217, especially paragraphs 0030 and 0031, and those set forth in Appendix A hereto.

Photosynthetic microorganisms include bacteria, algae, and molds having biocatalytic activity activated by light radiation. Examples of photosynthetic microorganisms for higher oxygenated organic compound production include, but are not limited to alga such as Bacillariophyceae strains, Chlorophyceae, Cyanophyceae, Xanthophyceaei, Chrysophyceae, Chlorella (e.g., Chlorella prototheocoides), Crypthecodinium, Schizocytrium, Nannochloropsis, Ulkenia, Dunaliella, Cyclotella, Navicula, Nitzschia, Cyclotella, Phaeodactylum, and Thaustochytrids; yeasts such as Rhodotorula, *Saccharomyces*, and Apiotrichum strains; and fungi species such as the Mortierella strain. Genetically enhanced photoautotrophic cyanobacteria, algae, and other photoautotrophic organisms have been adapted to bioconvert carbohydrates internal to the microorganism directly to ethanol, butanol, pentanol and other higher alcohols and other biofuels. For example, genetically modified cyanobacteria having constructs comprising DNA fragments encoding pyruvate decarboxylase (pdc) and alcohol dehydrogenase (adh) enzymes are described in U.S. Pat. No. 6,699,696. Cyanobacteria are photosynthetic bacteria which use light, inorganic elements, water, and a carbon source, generally carbon dioxide, to metabolize and grow. The production of ethanol using genetically engineered cyanobacteria has also been described in PCT Published Patent Application WO 2007/084477.

Process Discussion i. Feedstocks and Bioproducts

The feedstock can be liquid, gaseous or mixed phase. Where liquid, the feedstock need not be aqueous since the aqueous environment within the biocatalyst protects the microorganisms while the mass transfer substrate occurs from the non-aqueous phase to the biocatalyst.

Gas Phase

The processes can be used in a wide variety of applications, for instance, for the removal of components from gases for environmental, health and safety reasons; for improving the gases for downstream use such as removal of impurities and removal of co-reactants or catalyst poisons; and for converting substrate to desired bioproduct. Some specific examples include, but not in limitation, the treatment of flue gases and combustion gases to bioconvert and remove nitrogen oxides, sulfur oxides, carbon monoxide, carbon dioxide, halocarbons, volatile metal compounds, e.g., volatile mercury compounds emanating from the combustion of coal in power plants, and the like; treatment of industrial waste gases, including from refinery, petrochemical, manufacturing and coating operations; remediation of air in buildings; treatment of natural gas and biogas to remove undesired components such as sulfur compounds, nitrogen compounds and carbon dioxide; and bioconversion of gaseous substrates such as hydrogen, carbon monoxide, carbon dioxide, lower aliphatic compounds such as methane, ethane, propane and oxygenated compounds, to bioproducts such as higher hydrocarbons, oxygenated hydrocarbons such as alcohols, aldehydes, ketones, ethers, esters and acids which bioproducts may be used as biofuel, intermediates in other chemical processes or as final products.

Examples of substrate that may be contained in a gas phase include, but are not limited to, hydrogen, carbon monoxide, carbon dioxide, nitrogen oxides, ammonia, hydrogen sulfide, sulfur oxides, carbon disulfide, phosphine, carbonyls (such as phosgene and carbonyl sulfide), halocarbons (such as carbon tetrachloride and tetrafluoromethane), sulfur compounds (such as mercaptans and thioethers), volatile organic compounds (such as lower alkanes, lower alkenes, lower alkynes, aromatic organic compounds, alkanols, phenols, tetrahydrofurans, aldehydes, ketones, ethers, epoxides and halo-containing organic compounds, and volatile metal compounds including, but not limited to, heavy metals such as chromium, mercury, cadmium, radon, uranium, and selenium).

The gas in which the substrate is contained is not critical to the invention provided that the gas is not unduly adverse to the biocatalyst. Hence, the processes, as stated above, can be applicable to a broad range of uses. The processes of this invention can effectively treat gases containing virtually any concentration of substrate ranging from very low concentrations, e.g., even less than 1 part per million by volume, and sometimes less than 10 parts per billion by volume. The gas may be composed essentially entirely of substrate. For instance, in an anabolic conversion of carbon dioxide to bioproduct or methane to bioproduct, high concentrations of substrate are not only useable but are often available. The one or more components of the gas phase that are not substrate may be combined with the substrate to provide the feedstock for the bioconversion or may inherently contain the substrate, e.g., such as would be the case with a flue gas, industrial waste gas, and air requiring remediation.

Typically the gas phase contains water vapor. Preferably the relative humidity of the gas phase provided for contact with the matrices at the temperature and pressure conditions of the contact is between about 50 to slightly supersaturated, preferably between about 70 and 100 percent. In some instances, a water vapor may be added to the gas phase to obtain the desired relative humidity. Preferably the gas phase does not contain a concentration of components other than the substrate that during the contact with the matrices will result in condensation of liquid on the surface of the matrices. In some instances, a diluent may be added to the gas phase to reduce the partial pressure of the condensable component and thereby attenuate the risk of forming such condensate on the surface of the matrices. Alternatively, the exterior of the biocatalysts may be at least partially coated with a liquid hydrophobic layer that has high sorption for the substrate.

The gas phase may contain more than one substrate. In some instances, the two or more substrates present may be able to be bioconverted by a single species of microorganism contained in the biocatalyst. For example, microorganisms have been proposed that are capable of converting hydrogen and carbon dioxide to ethanol as well as converting carbon monoxide to ethanol. Similarly, microorganisms have been proposed that are capable of converting nitrogen oxides to nitrogen. Since the microorganisms are substantially irreversibly retained in the biocatalyst, the processes of this invention also contemplate the use of a mixture of biocatalysts containing different bioactive materials. Thus, for instance, a flue gas from a coal-fired power plant that contains both nitrogen oxides and volatile mercury compound can be contacted with a mixture of biocatalysts from one group of which contains microorganisms suitable for the bioconversion of nitrogen oxides to nitrogen and the other group of which contains microorganisms suitable for the reduction of the volatile mercury compound and sequestration of the mercury. Similarly, a mixture of biocatalysts or a mixture of bioactive materials in a biocatalyst may be used where one substrate is converted by one bioactive material to a substrate used by another bioactive material for energy or in the bioconversion pathway. By way of example, a photosynthetic microorganism may convert carbon dioxide to a hydrocarbon-containing bioproduct which is consumed by another microorganism performing a bioconversion on another substrate in the gas, e.g., conversion of nitrogen oxides to nitrogen or reducing volatile mercury compounds.

In some instances, the gases containing substrate may also contain components that may be adverse to the bioactive material. Although often the biocatalyst exhibits enhance the resistance to such toxins, it may be desired to pretreat the gases to reduce the concentration of such toxins. The pretreatment may comprise any suitable unit operation including, but not limited to, sorption, chemical reaction, membrane separation, ultrafiltration, and metabolic treatment.

The biocatalysts facilitate the mass transfer of the substrate from the feedstock to the bioactive material. In part, this facilitation is because the gas phase contacts the biocatalyst directly. The mass transfer into the interior of the biocatalyst may be via diffusion through the aqueous liquid in the pores, and may be, especially with substrate having limited solubility in water, such as nitrogen oxides and hydrocarbons, though diffusion or permeation through the polymer of the biocatalyst. The high hydraulic expansion of the polymer means that the polymer has little crystallinity which enhances permeability. The mass transport mechanism is believed to enable a gas phase bioreactor to bioconvert substrate that is in low concentration in the gas phase, e.g., less than about 1 part per million by volume, and that is in high concentration in the gas phase, e.g., up to 100 volume percent, yet still achieve a high conversion of the substrate to bioproduct. For example, nitrogen oxides may be present in a gas the amount of 1 or more volume percent, but the processes of this invention may provide an effluent containing less than 10 percent of that initially present. The high degree of hydraulic expansion also indicates that the distance between the surface of the biocatalysts and the biocatalysts retained therein can be relatively thin, frequently less than about 25, preferably less than about 10, microns, which also enhances the rate of mass transfer.

The biocatalysts retain aqueous medium, and nutrients where required to sustain the microorganisms, during contact with the gas phase, and the hydrated, hydrophilic polymer assists in providing moist microenvironments. Accordingly, the biocatalysts can be retained in contact with gas phase, including gas phase with low relative humidity, for extended periods of time without adversely affecting the biocatalyst, including where the biocatalyst comprises microorganisms. Often, the duration of contact with the gas phase may be greater than about 30 minutes, and sometimes as long as 10 hours or more, frequently between about 1 and 6 hours. As the biocatalysts have a high HEV, the biocatalysts can lose water during the contact with the gas phase while still retaining sufficient water for the viability of the bioactive material. The biocatalysts having reduced hydration, when immersed in the aqueous medium of the immersion step, regain hydration and maintain physical strength.

Liquid Phase

Where the feedstock is liquid, it may be aqueous or substantially nonaqueous and may contain dissolved gases or liquids containing dispersed gases therein of the type described above with respect to gas phase. Preferably, where the fluid is nonaqueous, these substrates are more polar compounds such as alcohols, aldehydes, ketones, carbohydrates, oxyanions (including but not limited to, sulfoxy moieties, metalates, phosphates, sulfides, mercaptans, amines, amides); and the like.

Examples of anabolic or catabolic processes suitable to be practiced by the processes of this invention include, but are not limited to, and:

Nitrates, perchlorates, taste and odor compounds, organics, chlorinated hydrocarbons, and the like removal from the water. The source of the water may be from a water treatment facility, ground sources, surface sources, municipal wastewater processing, and industrial waste water. The water stream may be derived from other bioconversion processes where substrate is not fully consumed, such as in corn ethanol processes.

Carbohydrate, including, but not limited to cellulose, hemicellulose, starches, and sugars for conversion to hydrocarbons and oxygenated organic product.

Oxyanions, hydroxyls or soluble salts of sulfur, phosphorus, selenium, tungsten, molybdenum, bismuth, strontium, cadmium, chromium, titanium, nickel, iron, zinc, copper, arsenic, vanadium, uranium, radium, manganese, germanium, indium, antimony mercury, and rare earth metals for removal from water by bioconversion and sequestration.

ii. Zones, Vessels and Bioreactors

The processes of this invention involve cycling biocatalyst between at least two different media. As stated above, the process may be conducted in a single vessel or in a plurality of vessels, each of which may perform a different function. Different functions may be performed in a single vessel, and a vessel may have different zones. In the processes, a sorption zone is used for contact with the feedstock. At least one ancillary zone is provided to perform a function facilitating the bioconversion as described above.

The vessels (herein referred to as reactors) used for each zone may be of any suitable configuration to effect the function and to permit the cycling of biocatalyst. Such configurations include, but are not limited to, bubble column reactors, stirred reactors, packed bed reactors, trickle bed reactors, fluidized bed reactors, plug flow (tubular) reactors, and membrane (biofilm) reactors. In conducting photosynthetic bioconversions, the reactors may be designed to permit the transfer of photo energy. The biocatalyst may be freely mobile in the reactor or fixed, e.g., to a structure in the reactor vessel, or may itself provide a fixed structure. More than one reactor vessel may be used for accomplishing the function of the zone. For instance, reactor vessels may be in parallel or in sequential flow series. The biocatalysts may be in a shallow moving bed or ebulating bed to permit illumination from above the biocatalysts.

Because the biocatalysts contain a high density of bioactive material, they may be started-up quickly. Moreover, the biocatalyst may not require that the reactor be sterilized prior to use.

Sufficient water is provided to the biocatalyst to maintain the biocatalyst hydrated in at least one zone. Water may be provided from any suitable source including, but not limited to, tap water, demineralized water, distilled water, and process or waste water streams. The water or other media contacting the biocatalyst in the cyclic process can contain nutrients and additives such as growth promoters, buffers, antibiotics, vitamins, minerals, nitrogen sources, and sulfur sources for any microorganisms that are used as microorganisms as is known in the art. If desired, an antifoam agent may be used in the aqueous medium.

In some instances, where additives such as potentiators, enhancers and inducers are desired or required for the metabolic process, the biocatalysts of this invention exhibit at least equivalent bioconversion activity at a lesser concentration of such additives as compared to a planktonic system, all else being substantially the same. Thus operating costs can be reduced.

iii. Sorption Zone

The processes of this invention use a sorption zone for contact with the feedstock. The temperature and pressure conditions within the sorption zone may fall within a wide range; however conditions that are not unduly deleterious to the bioactive material and that favor the sorption of substrate into the biocatalyst are preferred. In some instances the temperature is suitable for metabolic activity; however, temperatures can be used that enable little, if any, bioconversion to occur provided that the temperature does not destroy the bioactive material. The biocatalysts that contain microorganisms, due to the phenotypic changes and communications among the community, are capable of tolerating a broader range of temperatures than where planktonic. Often the temperature within the sorption zone is in the range of about 5° C. to 75° C. or 100° C. or more, say, about 10° C. to 65° C.

In continuous processes, the pressure at the location of the exit of substrate-depleted feedstock from the sorption zone is frequently in the range of between about 50 and 5000, preferably, 70 to 500, kPa absolute. Similarly the flow rate of the feedstock can fall within a wide range. The flow rate of the feedstock may, for if desired, be sufficient to provide an expanded or fluidized bed of the biocatalyst. On the other hand, where the biocatalyst is a fixed. moving, packed bed, a substantially lesser flow rate may be desirable. For feedstocks that are liquid, the liquid hourly space velocity is typically in the range of about 0.1 to 10 reciprocal hours; and for feedstocks that are gaseous, the gas hourly space velocity is typically in the range of about 10 to 1000 reciprocal hours.

The flow of the feedstock through the sorption zone, preferably, should not result in channeling our other maldistribution of the fluid. The aspect ratio of the sorption zone, the presence of baffles or other flow diverters, and fluid distribution devices can be selected as known to those skilled in the art to provide desired uniformity of distribution within the sorption zone. Also, where the biocatalyst is deformable, the bed height should not be so great as to cause deformation that occludes flow channels. Often the height of a bed of biocatalyst is less than about 5 meters, and in some instances less than about 3 meters.

In many instances, the average retention time of the biocatalyst in the sorption zone is sufficient to sorb at least about 50, sometimes at least about 70, percent of the substrate contained in the feedstock. The average retention time may vary from between about 10 seconds to one or two days, say between about 30 seconds to 5 hours. The average retention time should not be so long as to unduly adversely affect the bioactive material contained in the biocatalyst due to a lack of contact with the aqueous medium or nutrients. Where the biocatalysts contain microorganisms, the phenotypic changes and communications among the population of microorganisms enable the biocatalyst to enter an essential stasis condition. Hence, in one aspect, the sorption step can occur while the microorganisms are in a state of stasis. Especially where the metabolic process is an anabolic process, the duration of the average retention time should not result in significant amounts of bioproduct being produced and released within the sorption zone unless intended.

iv. Bioconversions

Bioconversion conditions are maintained for conversion of at least one substrate to at least one chemical product including conditions of temperature, pressure, oxygenation, pH, and nutrients and additives. The bioconversion may be on a continuous, semi-continuous or batch mode of operation.

The processes may be conducted with all carbon requirements being provided in the aqueous medium or on a carbon source deficient basis where a polysaccharide is included in the biocatalyst. Where operating in a carbon source deficiency, the aqueous medium often provides at least about 50, frequently at least about 75, say, 80 to less than 100, mass percent on a carbon basis of the carbon nutrient.

The bioconversion processes may be optimized to achieve one or more objectives. For instance, the processes may be designed to provide high conversions of substrate to bioproduct or may be designed to balance capital and energy costs against conversion to bioproduct. As the biocatalysts are highly hydrated, generally their density is close to that of water. Accordingly, with fluidized bed reactor designs using an aqueous feed stream, energy consumption is lower than that where higher density supports are used. In some instances where the metabolic processes generate a gas, e.g., in the conversion of sugars to alkanols or in the bioconversion of nitrate anion to nitrogen gas, gas can accumulate in the biocatalyst to increase buoyancy. This accumulated gas can reduce the energy consumption for a fluid bed operation and can facilitate the use of other bioreactor designs such as jet loop bioreactors.

The bioproduct may be recovered from the aqueous medium in any suitable manner including the Typical Separation Techniques.

v. Cyclic Sorption and Bioconversion with Transport of Biocatalysts

This aspect of the processes of the invention will be further described in connection with FIGS. 1 and 2. FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also all omits ancillary unit operations. The apparatus depicted in FIG. 1 may be used to recover substrate from gaseous streams or liquid streams. The following discussion will illustrate both modes of operation.

Feedstock containing substrate is provided via line 102 to sorber column 104. As depicted sorber column 104 provides for countercurrent contact between a moving bed of biocatalyst and the feedstock. In sorber column 104 substrate is selectively sorption in the biocatalyst for later bioconversion to a degradation bioproduct or anabolic bioproduct. Feedstock having depleted substrate content exits sorber column 104 via line 106. Where the feedstock is gaseous usually the high hydration of the biocatalyst does not necessitate any rehydration in sorber column 104. FIG. 1 illustrates an option to provide a spray of aqueous medium to maintain the biocatalyst wet. As shown, aqueous medium can be provided via line 108 to sorber column 104.

Biocatalyst is passed from sorber column 104 to metabolic reaction vessel 110. The biocatalyst may be directly introduced into reaction vessel 110, especially where no solids or debris deposit on the biocatalyst. In some instances, it may be desired to treat the biocatalyst prior to their introduction into the reaction vessel 110. For example, the sorption zone may be operated under aerobic conditions but the reaction vessel may be operating under anaerobic or anoxic conditions. In such situations, removal of oxygen from the interstitial spaces among the biocatalyst by purging, vacuum, washing with deaerated water, and the like reduces the amount of adventitious oxygen passing to the aqueous medium in reaction vessel 110. Where the feedstock being passed through the sorption zone is a liquid, it is usually desire to remove excess liquid from the biocatalyst prior to being introduced reaction vessel 110. The removal of the liquid may be by any convenient means, including but not limited to, washing or rinsing, filtering or screening to separate liquid phase from the biocatalyst, centrifugation, and the like. Where the surface of the biocatalyst has been contaminated with solids or liquids not desired in reaction vessel 110, washing or rinsing, e.g., with water, may be desired.

The withdrawal of the biocatalyst from sorption zone 104 may be on a continuous or discontinuous basis as desired. The biocatalyst may be transported by any convenient means, including, as a pumped slurry, by a screw conveyor, belt conveyor, and the like. In general, the duration between the withdrawing biocatalyst to its introduction in reaction vessel 110 is less than about 2 hours, preferably less than about 30 minutes.

As shown, line 120 passes biocatalyst to washing operation 122. Washing operation 122. A washing liquid such as water is provided via line 124 to washing operation 122 and the washing fluid is discharged via line 126. The washed biocatalyst withdrawn via line 128 and passed to hydrocyclone 130 for the separation of the biocatalyst from the incipient liquid. Hydrocyclone 130 and washing operation 122 may in some instances not be required, and in other instances only one of the two operations may be needed. The separated biocatalyst is passed via line 132 to reaction vessel 110. Line 132 may be a conveyor such as a belt conveyor or screw conveyor. Removed liquid is withdrawn from hydrocyclone 130 via line 134.

Reaction vessel 110 contains aqueous media and biocatalyst. The aqueous medium contains nutrients (including carbon source if not provided by the substrate) and optionally other adjuvants to support the metabolic processes. Reaction vessel 110 is maintained under conditions suitable for the metabolic activity. In the reaction vessel 110 bioproducts are passed from the biocatalyst into the aqueous medium. The average residence time of the biocatalyst in the reaction vessel may fall within a wide range, but preferably is sufficient to reduce the concentration of the bioproduct in the biocatalyst by at least about 50, preferably at least about 70, percent. Frequently, the average residence time ranges between about 10 minutes to 24 hours or more.

Reaction vessel may contain two or more bioactive materials, at least one of which is contained in the biocatalyst. Also two or more different biocatalysts may be used wherein the different biocatalysts contain different bioactive materials.

The biocatalyst is typically withdrawn from the reaction vessel in combination with aqueous medium, and the aqueous medium is preferably removed from the biocatalyst and recycled back to the reaction vessel to conserve nutrients and other adjuvants. As depicted, a portion of the aqueous media is withdrawn via line 112 and passed to liquid solid separator 114. Liquid solid separator 114 may be any suitable apparatus for separating biocatalyst from aqueous medium such as, but not limited to, filtration screens, settling tanks, hydrocyclones, and the like. The fraction containing the biocatalyst is passed from liquid solid separator 114 via line 116 to sorber column 104. Line 116 is usually a conveyor, including but not limited to, screw conveyors and belt conveyors. Preferably the unit operation to separate the biocatalyst from the aqueous medium provides the biocatalyst a point of incipient wetness. If desired, the biocatalyst may be washed or rinsed prior to being introduced into sorber column 104.

Where the process is operated on a continuous basis, the rates that the biocatalyst passed to the sorption zone should balance with the rate that the biocatalyst is returned to the reaction zone from the sorption zone.

The biocatalyst in sorber column 104 passes downwardly and is removed a lower portion of the column. The average residence time of the biocatalyst in sorber vessel 104 is typically sufficient to substantially reduce the concentration of the substrate in the feedstock.

Figure 2:
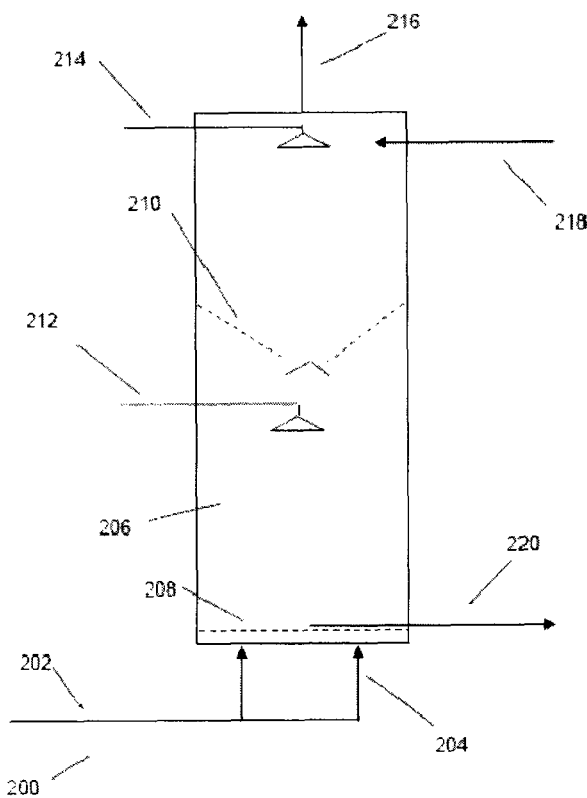
FIG. 2 is a schematic depiction of a sorption vessel that can be used in the apparatus and processes of this invention.

With reference to FIG. 2, a sorber assembly generally indicated by the 200 is depicted. Sorber assembly 200 is particularly adapted for use with gaseous feed streams containing substrate to be recovered while maintaining the biocatalyst moist. The gaseous feed stream is provided by line 202 and is distributed via lines 204 to lower portion of sorber column 206. Sorber column 206 contains porous plate 208 in the bottom portion. The openings in porous plate 208 are sufficiently small that the biocatalyst is retained above the porous plate. Sorber column 206 also contains baffle mechanism 210 in a mid-portion. Baffle mechanism 210 comprises a downwardly pointed conical, porous structure through which up flowing gases can pass while retaining biocatalyst. The biocatalyst flows to a lower portion of the conical baffle and is distributed below. Two aqueous spray units are provided within sorber column 206, spray unit 212 and spray unit 214. Spray unit 214 is adapted to maintain the biocatalyst above baffle mechanism 210 wet. Spray unit 212 is adapted to maintain the biocatalyst below baffle mechanism 210 wet. The water from the aqueous spray may also sorb substrate and may be recycled for contact with the biocatalyst or used as an aqueous medium in a bioreactor. Gas having a reduced concentration of substrate exits sorber column 206 via line 216. Biocatalyst for sorbing substrate is provided to an upper portion of sorber column 206 via line 218, and biocatalyst containing sorbed substrate are withdrawn from a lower portion of sorber column 206 via line 220.

vi. Gas Phase System

The gaseous phase containing the substrate is contacted under metabolic conditions with the biocatalyst for the bioconversion. The biocatalyst may be in a fixed bed configuration during the passage of the gas phase through the bed or may be subject to movement during the contact such as a moving bed or a bed that is at least partially suspended by the gases.

Preferably, at least a portion of the biocatalyst surrounded by the gases to enhance a more uniform distribution of the gas phase through the bed and to enhance the surface area of the matrices available for contact with the gas phase. Thus at least a portion of the biocatalyst is in the discontinuous phase during the contacting. Preferably, at any given time during the contacting at least about 50, say, between about 70 and essentially all the biocatalyst is in the discontinuous phase.

Frequently, the superficial velocity of the gas phase is an important parameter affecting the performance of the biocatalyst. The superficial velocity of the gas phase will affect the intermixing of the gas phase as substrate is removed by the biocatalyst for bioconversion and thus minimize the presence of stagnant regions. Where the bed of biocatalyst is at least partially suspended by the flow of the gas phase, the superficial velocity of the gas phase should be sufficient to provide the sought degree of suspension. The superficial velocity gas phase can readily be determined by those of ordinary skill in the art taking into account the size of the biocatalyst, the density of the biocatalyst, and the configuration of the bioreactor. In general, the superficial velocity of the gas phase for fluidized bed reactors is in the range of between about 0.25 to 5, say 0.3 to 2, meters per second. Riser reactors often operate with superficial velocities in the range of about 0.5 to 10 meters per second.

The duration that biocatalyst is subjected to the contact with the gas phase may also be affected by the build-up, if any, of bioproducts in the biocatalyst, especially bioproducts that can be adverse to the bioconversion at higher concentrations. With some catabolic processes, e.g., the bioconversion of nitrogen oxides to molecular nitrogen, the bioproduct can pass to the gas phase and be removed from the biocatalyst. In other processes such as for the metabolic reduction of volatile metal compounds and the anabolic generation of liquid bioproducts, it may be necessary to cease the gas phase contact for removal of the bioproducts before they reach a level that may be adverse to the bioconversion.

Gas phase systems in accordance with this invention are described in connection with FIGS. 3, 4 and 5. These Figures are schematic depictions of apparatus suitable for practicing the processes of this invention. The Figures also omit minor equipment such as pumps, compressors, valves, instruments and other devices the placement of which and operation thereof are well known to those practiced in chemical engineering. The Figures omit ancillary unit operations.

Figure 3:
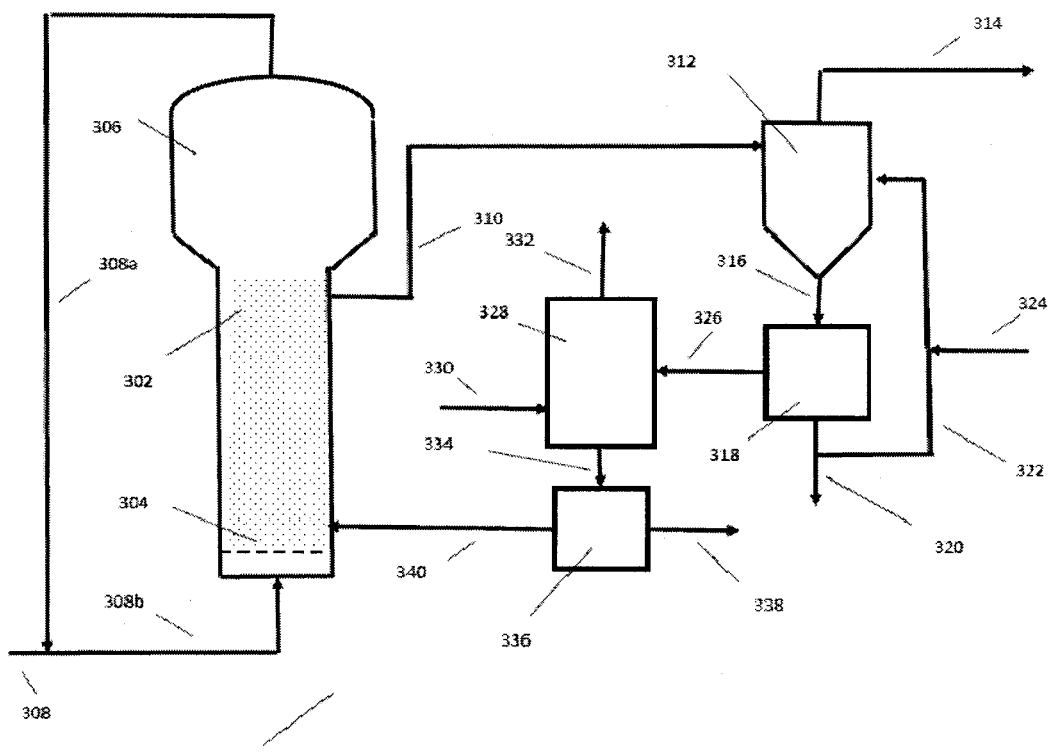
FIG. 3 is a schematic drawing of an apparatus suitable for conduction the processes of this invention where the contact between the gas phase and biocatalyst is conducted in a fluidized bed.

FIG. 3 schematically depicts an apparatus generally designated as 300 in which the biocatalyst is retained in a fluidized bed for contact with the gas phase. Fluidized bed reactor 302 is provided with a gas distributor 304 at a bottom portion and expanded section 306 at the top where biocatalyst can be disentrained. The gas phase containing the substrate to be treated is introduced into reactor 302 at the bottom via line 308. The gas phase passes through gas distributor 304 and flows generally upwardly through a reactor 302 and a velocity sufficient to fluidize the biocatalyst. As shown, gas phase is withdrawn from the top of expanded section 306 via line 308a for recycle. The gas in line 308a is combined with fresh gas phase from line 308, and the combined gases are passed via line 308b to the bottom of reactor 302.

As shown, the gas phase exits reactor 302 at about the upper boundary of the fluidized bed via line 310. The exiting gas phase contains entrained biocatalyst and is passed to cyclone 312 for separation of biocatalyst from the gas phase which exits cyclone 312 via line 314. If adequate bioconversion of substrate contained in the gas phase has occurred, the gas phase may be passed to additional unit operations or discharged. In some instances it may be desired to return a portion of the gas phase to reactor 302 for additional bioconversion of substrate. Alternatively, another gas phase bioreactor may be in flow sequence, and the gas phase in line 314 is passed to that reactor.

The biocatalyst that has been in contact between the gas phase must from time to time be rehydrated. During this period of time a number of other operations may occur such as replenishment of nutrients where the biocatalyst comprises microorganisms; removal of bioproduct for recovery or other metabolites or waste products from the bioconversion; and removal of debris and contaminants, including contaminating microorganisms, from the surface of the biocatalyst. Accordingly, the biocatalyst may be contacted one or more liquid media during this period. While it is preferable, it is not essential for the passage of the gas to cease during the contact with one or more liquid media.

The contact with one or more liquid media may occur in the same vessel as the contact with the gas phase or the biocatalyst may be transported to one or more separate vessels for contact with liquid media. Where the biocatalyst is retained in the same vessel used for contacting with the gas phase, it may be desired to provide two or more vessels such that at least one vessel will be used for the contact of biocatalyst with the gas phase while at least one other vessel is being subjected to one or more operations using liquid media. Preferably, especially for processes in which at least a portion of the biocatalyst is suspended during the contact with the gas phase, a portion of the biocatalyst is withdrawn on an intermittent or continuous basis from the vessel used for the gas contact for processing using at least one liquid medium. The rate of withdrawal of the biocatalyst can readily be determined by one of ordinary skill in art to achieve an average residence time for contact with the gas phase that provides both acceptable bioactivity and avoidance of undue dehydration of the biocatalyst.

As shown the biocatalyst is discharged from cyclone 312 via line 316 and are directed to bioproduct recovery vessel 318. Where the operation of the apparatus is intended to convert substrate to a gas such as nitrogen, carbon dioxide, or methane, bioproduct recovery vessel 318 may not be employed. However, vessel 318 may serve as a washing vessel to remove debris that may have accumulated on the surface of the biocatalyst. For instance, an aqueous wash system may be used, and the washing vessel 318 may contain a screen or other barrier to separate the biocatalyst from spent aqueous wash liquid containing removed debris. The separated, spent aqueous wash liquid exits vessel 318 via line 320. A portion of the spent aqueous wash liquid may be reused, and, as depicted, passed via line 322 for recycle. Fresh makeup water can be provided via line 324. The wash liquid may be directly introduced into washing vessel 318 or may be introduced into cyclone 312 to assist in removal of the biocatalyst from cyclone 312. The contact of the liquid medium with the biocatalyst for washing may be by any convenient means. For instance, liquid medium may be sprayed onto the biocatalyst or the biocatalyst may be immersed in a volume of the liquid medium. The type of contact of the liquid medium with the biocatalyst will in part depend upon the operation to be effected. For instance, where the operation is primarily to effect removal of debris from the surface of the biocatalyst, a spray or liquid-solid contact having a sufficient relative velocity may be desired to provide physical forces assisting in the removal of the debris. On the other hand, a hydration operation may not require a relative movement between the liquid medium and the biocatalyst for obtaining desired performance. Where the contact between the liquid medium and the biocatalyst involves immersion of the biocatalyst, the biocatalyst may be in, by way of example and not in limitation, a packed bed, trickle bed, stirred bed, fluidized bed, moving bed, or pumped slurry bed. The contact between the liquid medium in the biocatalyst may thus be a co-current, countercurrent, cross current, or indeterminate such as with a fluidized bed.

The aqueous medium in vessel 318 will also serve to rehydrate the biocatalyst. The minimum duration of the contact for hydration should be sufficient to maintain a steady-state, continuous process, i.e., avoid a net loss of water from the biocatalyst. Since the biocatalyst is composed of highly hydrophilic polymer, often the hydration may be achieved quickly, e.g., within about 1 to 250 seconds. The temperature and pressure for the hydration step may fall within a wide range. In some instances, the biocatalyst may be cooled from the temperature of the contact with the gas phase. The cooling may reduce the metabolic activity of the microorganisms where the biocatalyst comprises microorganisms thus providing prolonged stability of the population of microorganisms in the biocatalyst in the absence of gas a substrate. Often, however, the contacting with the aqueous medium is at the ambient temperature of the aqueous medium thereby avoiding costs associated with equipment to maintain the aqueous medium at a given temperature. In general, the temperature of the contacting is in the range of between about 0° C. and 80° C. Typically, the pressure is in the range of between about 50 and 5000 kPa.

Where vessel 318 is used for bioproduct recovery, bioproduct contained in the biocatalyst diffuses into the aqueous medium in vessel 318. Typically the driving force for the diffusion of the bioproduct is based upon the relative concentrations of the bioproduct in the aqueous medium and in the biocatalyst. Although one stage is shown for bioproduct recovery, is to be understood that two or more sequential stages may be used. The use of two or more sequential stages is particularly advantageous when a high concentrate stream of bioproduct is sought to reduce recovery costs and a low concentration of bioproduct is desired in the biocatalyst to be returned to reactor 302. Inherently the bioproduct recovery may serve to remove at least some debris from the surface of the biocatalyst, and the aqueous stream exiting vessel 318 may be subjected to filtration or other unit operation to remove solids from the aqueous stream prior to recovery of the bioproduct. The recovery of the bioproduct may be by any convenient unit operation including, but not limited to, Typical Separation Techniques.

In one mode, a separate operation is used for bioproduct recovery is used and involves maximizing the concentration of the sought bioproduct in a liquid medium. This maximization can be achieved by using a limited amount of liquid medium and maintaining the contact with the biocatalyst for sufficient period of time to approach equilibrium the concentration of the biocatalyst. Several stages of contact or counter current contact may be employed to provide a highly concentrated liquid product stream. In some instances it may be possible to use as a liquid medium an extracting solvent for the bioproduct. Thus, the liquid medium maybe aqueous, may be a mixture of water and extracting solvent, or may essentially comprise an extracting solvent. The extracting solvent should not be unduly deleterious to the bioactive material. The liquid medium may contain co-solvents, coupling agents, or other additives to enhance the recovery of bioproduct and other metabolites from the biocatalyst. Components, which may be used as the liquid medium or dissolved in or emulsified with water, may include by way of example, and not in limitation, oxygenated hydrocarbons such as alkanols, esters, ethers, and ketones of 1 to 100 carbon atoms; hydrocarbons of 1 to 100 carbon atoms; amines; amides; and phosphates.

The bioproduct recovery may also be by chemical treatment of the biocatalyst. For instance, where the biocatalyst are used to remove components from the gas phase via reduction such as removal of volatile organometallic components or sulfur oxides, the reduced metal component or sulfur component may oxidized to facilitate its removal from the biocatalyst.

The conditions for the contacting of the liquid medium with the biocatalyst for the removal of bioproducts will depend upon the nature of the biocatalysts, the concentration of the bioproducts in the biocatalyst and desired concentration of the bioproducts after the contacting, the nature of the liquid medium and the like. The duration of such operation may often be in the range of between about 1 minute to 5 or more hours. The conditions of temperature and pressure should be appropriate for the microorganisms and are often in the range of between about 0° C. and 80° C. and about 50 and 5000 kPa.

Preferably at least one operation involving contact with liquid media serves to replenish nutrients, carbon source or other adjuvants (replenishment components) to the biocatalyst. Some replenishment components may be provided in the gas phase but often are provided by a liquid contact operation. The type and amount of replenishment components can readily be determined by one of ordinary skill in the art. The replenishment components may be supplied during the hydration, or it may be a separate step.

One or more subsequent bioconversions beyond bioconversion of the substrate in the feedstock may occur during the cycling of the biocatalyst. Such subsequent bioconversions may be to accomplish one or more objectives. For instance, the metabolic activity may serve to provide energy to the microorganisms and thus enhance their vitality during the duration of the contact with the gas phase. The metabolic activity may serve to accumulate a metabolic intermediate for further bioconversion when contacted with the gas phase containing substrate. Alternatively, the metabolic activity may be the bioconversion of a metabolic intermediate produced during the contact with the gas phase. These sequenced metabolic processes can be useful in producing secondary metabolite bioproducts.

As depicted, the biocatalyst is passed from vessel 318 to vessel 328 via line 326. Vessel 328 contains an aqueous medium and serves to provide nutrients to the biocatalyst and, if not already accomplished in vessel 318, rehydrate the biocatalyst. In some instances, the metabolic activity may be occurring in vessel 328. An aqueous stream containing nutrients to be supplied to the biocatalyst is provided via line 332 vessel 328. Line 332 is provided at the top of vessel 328 to allow for the discharge of any evolved gases from the biocatalyst.

The biocatalyst is then passed from vessel 328 via line 334 to separator 336. Separator 336 serves to recover aqueous medium from the exterior of the biocatalyst, which aqueous medium is discharged via line 338. The separated biocatalyst is directed via line 342 the bottom portion of reactor 302 wherein the biocatalyst are re-fluidized. In a typical operation, a balance exists between the degree of removal of free water on the surface of the biocatalyst and the processing required to achieve that removal of free water. Consequently, in many instances, the biocatalyst being reintroduced into reactor 302 contains some free liquid on the surface.

Figure 4:
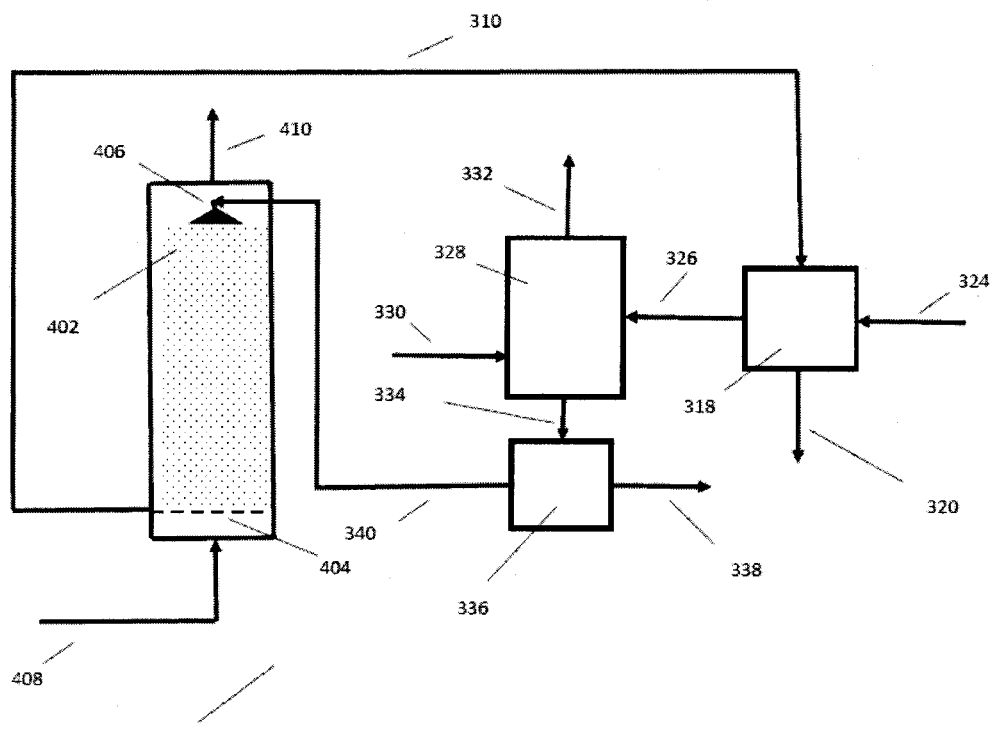
FIG. 4 is a schematic drawing of an apparatus suitable for conduction the processes of this invention where the contact between the gas phase and biocatalyst is conducted in a moving bed.

FIG. 4 depicts another apparatus generally designated as 400 that is suitable for practicing the processes of this invention in which a moving bed reactor is used. Components designated by the same number as the components in FIG. 3 are the same. Moving bed reactor 402 has screen plate 404 at a lower portion and distributor 406 at an upper portion for distributing the biocatalyst at the top of the moving bed. Line 408 supplies gas phase containing substrate to the bottom of reactor 402 for passage through screen plate 404 and the moving bed of biocatalyst above the screen plate. Reactor 402 is also provided with line 410 by which the gas phase, after contacting the biocatalyst, exits.

The bed of biocatalyst in reactor 402 flows downward and countercurrent to the direction of the gas phase passing therein. Reactor 402 may contain baffles in order to provide a more uniform rate of flow of the biocatalyst. Biocatalyst at the bottom of reactor 402 and immediately above screen plate 404 is withdrawn via line 310 and passed to vessel 318. Line 340 returns the biocatalyst to the top of reactor 302 where they are distributed by distributor 306. Since the biocatalyst are withdrawn from a moving bed and thus have relatively little gas phase, the use of a cyclone such as described in the apparatus of FIG. 4 may often not be required.

Figure 5:
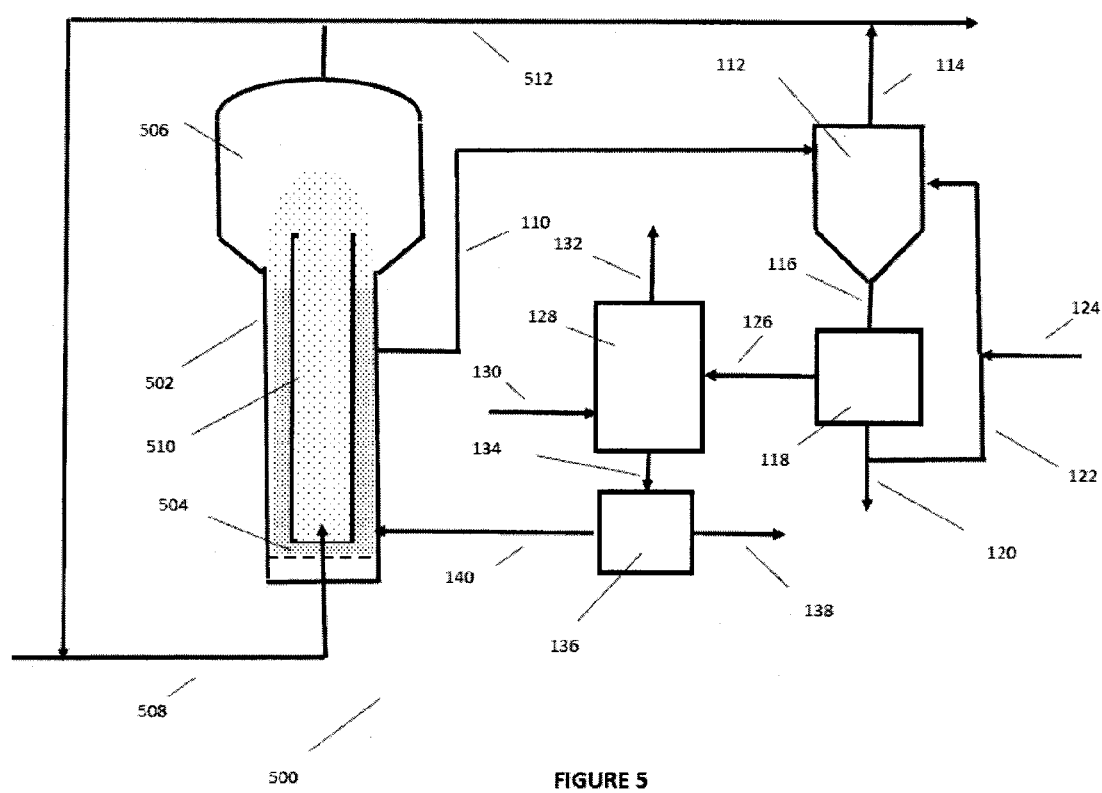
FIG. 5 is a schematic drawing of an apparatus suitable for conduction the processes of this invention where the contact between the gas phase and biocatalyst is conducted in a loop bed.

FIG. 5 depicts yet another apparatus generally designated as 500 that is suitable for practicing the processes this invention in which a loop reactor is used. As with FIG. 4, components designated by the same number as the components in FIG. 5 are the same. Loop reactor 502 has screen plate 504 located in a bottom section and expanded section 506 at the top to disentrain biocatalyst contained in the gas phase. Reactor 502 also contains one or more riser tubes 510 extending from a lower portion to an upper portion of the reactor. Gas phase containing substrate is passed into a lower portion of each riser tube 510. The velocity of the gas phase in a riser tube is sufficient to carry the biocatalyst through the tube to expanded section 506. The biocatalyst then falls by the force of gravity to form a denser bed in the region surrounding the riser tube and then to the bottom of reactor 502 where they are again entrained in the upwardly passing gas phase and sent through the riser tube. Gas phase, after passing through the riser tube is withdrawn via line 512 located at the top of expanded section 506. Line 512 is shown as having the capability of recycling gases to line 508 for recycle to reactor 502 and for removal of treated gas.

Biocatalyst is withdrawn via line 310 from the denser region within reactor 502 and processed as described in connection with the apparatus of FIG. 3. Line 340 returns the biocatalyst to a lower portion of reactor 502. The biocatalyst may be introduced into the denser bed or into the bottom of riser tube 510.

It is to be understood that the processes of this invention can be integrated with other processes such that a bioproduct may be used as a feedstock for a subsequent process, which may be a metabolic or chemical process, or a substrate may be derived from a another process to be converted to a bioproduct. The ability to use a gas phase bioconversion is particularly attractive for integration of such processes, especially with other bioconversion processes. For instance, at least a portion of the bioproduct from a gas phase bioconversion can be passed to an aqueous menstruum containing a different bioactive material or substrate contained in the gas phase being supplied to the gas phase bioconversion can comprise bioproduct from another metabolic process or both.

APPENDIX A

Representative microorganisms include, without limitation, Acetobacter sp., Acetobacter aceti, Achromobacter, Acidiphilium, Acidovorax delafieldi P4-1, Acinetobacter sp. (A. calcoaceticus), Actinomadura, Actinoplanes, Actinomycetes, Aeropyrum pernix, Agrobacterium sp., Alcaligenes sp. (A. dentrificans), Alloiococcus otitis, Ancylobacter aquaticus, Ananas comosus (M), Arthrobacter sp., Arthrobacter sulfurous, Arthrobacter sp. (A. protophormiae), Aspergillus sp., Aspergillus niger, Aspergillus oryze, Aspergillus melleus, Aspergillus pulverulentus, Aspergillus saitoi, Aspergillus sojea, Aspergillus usamii, Bacillus alcalophilus, Bacillus amyloliquefaciens, Bacillus brevis, Bacillus circulans, Bacillus clausii, Bacillus cereus, Bacillus lentus, Bacillus licheniformis, Bacillus macerans, Bacillus stearothermophilus, Bacillus subtilis, Beijerinckia sp., Bifidobacterium, Brevibacterium sp. HL4, Brettanomyces sp., Brevibacillus brevis, Burkholderia cepacia, Campylobacter jejuni, Candida sp., Candida cylindracea, Candida rugosa, Carboxydothermus (Carboxydothermus hydrogenoformans), Carica papaya (L), Cellulosimicrobium, Cephalosporium, Chaetomium erraticum, Chaetomium gracile, Chlorella sp., Citrobacter, Clostridium sp., Clostridium butyricum, Clostridium acetobutylicum, Clostridium kluyveri, Clostridium carboxidivorans, Clostridium thermocellum, Cornynebacterium sp. strain m15, Corynebacterium (glutamicum), Corynebacterium efficiens, Deinococcus radiophilus, Dekkera, Dekkera bruxellensis, Escherichia coli, Enterobacter sp., Enterococcus, Enterococcus faecium, Enterococcus gallinarium, Enterococcus faecalis, Erwinia sp., Erwinia chrysanthemi, Gliconobacter, Gluconacetobacter sp., Hansenula sp., Haloarcula, Humicola insolens, Humicola nsolens, Kitasatospora setae, Klebsiella sp., Klebsiella oxytoca, Klebsiella pneumonia, Kluyveromyces sp., Kluyveromyces fragilis, Kluyveromyces lactis, Kocuria, Lactlactis, Lactobacillus sp., Lactobacillus fermentum, Lactobacillus sake, Lactococcus, Lactococcus lactis, Leuconostoc, Methylosinus trichosporum OB3b, Methylosporovibrio methanica 812, Methanothrix sp. Methanosarcina sp., Methanomonas sp., Methylocystis, Methanospirilium, Methanolobus siciliae, Methanogenium organophilum, Methanobacerium sp., Methanobacterium bryantii, Methanococcus sp., Methanomicrobium sp., Methanoplanus sp., Methanosphaera sp., Methanolobus sp., Methanoculleus sp., Methanosaeta sp., Methanopyrus sp., Methanocorpusculum sp., Methanosarcina, Methylococcus sp., Methylomonas sp., Methylosinus sp., Microbacterium imperiale, Micrococcus sp., Micrococcus lysodeikticus, Microlunatus, Moorella (e.g., Moorella (Clostridium) thermoacetica), Moraxella sp. (strain B), Morganella, Mucor javanicus, Mycobacterium sp. strain GP1, Myrothecium, Neptunomonas naphthovorans, Nitrobacter, Nitrosomonas (Nitrosomonas europea), Nitzchia sp., Nocardia sp., Pachysolen sp., Pantoea, Papaya carica, Pediococcus sp., Pediococcus halophilus, Penicillium, Penicillium camemberti, Penicillium citrinum, Penicillium emersonii, Penicillium roqueforti, Penicillum lilactinum, Penicillum multicolor, Phanerochaete chrysoporium, Pichia sp., Pichia stipitis, Paracoccus pantotrophus, Pleurotus ostreatus, Propionibacterium sp., Proteus, Pseudomonas (P. pavonaceae, Pseudomonas ADP, P. stutzeri, P. putida, Pseudomonas Strain PS1, P. cepacia G4, P. medocina KR, P. picketti PK01, P. vesicularis, P. paucimobilis, Pseudomonas sp. DLC-P11, P. mendocina, P. chichhori, strain IST 103), Pseudomonas fluorescens, Pseudomonas denitrificans, Pyrococcus, Pyrococcus furiosus, Pyrococcus horikoshii, Ralstonia sp., Rhizobium, Rhizomucor miehei, Rhizomucor pusillus Lindt, Rhizopus, Rhizopus delemar, Rhizopus japonicus, Rhizopus niveus, Rhizopus oryzae, Rhizopus oligosporus, Rhodococcus, (R. erythropolis, R. rhodochrous NCIMB 13064), Salmonella, Saccharomyces sp., Saccharomyces cerevisiae, Schizochytriu sp., Sclerotina libertina, Serratia sp., Shigella, Sphingobacterium multivorum, Sphingobium (Sphingbium chlorophenolicum), Sphingomonas (S. yanoikuyae, S. sp. RW1), Streptococcus, Streptococcus thermophilus Y-I, Streptomyces, Streptomyces griseus, Streptomyces lividans, Streptomyces murinus, Streptomyces rubiginosus, Streptomyces violaceoruber, Streptoverticillium mobaraense, Synechococcus sp., Synechocystis sp., Tetragenococcus, Thermus, Thiosphaera pantotropha, Trametes, Trametes versicolor, Trichoderma, Trichoderma longibrachiatum, Trichoderma reesei, Trichoderma viride, Trichosporon sp., Trichosporon penicillatum, Vibrio alginolyticus, Xanthomonas, Xanthobacter sp. (X. autotrophicus GJ10, X. flavus), yeast, Yarrow lipolytica, Zygosaccharomyces rouxii, Zymomonas sp., Zymomonus mobilis, Geobacter sulfurreducens, Geobacter lovleyi, Geobacter metallireducens, Bacteroides succinogens, Butyrivibrio fibrisolvens, Clostridium cellobioparum, Ruminococcus albus, Ruminococcus flavefaciens, Eubacterium cellulosolvens, Clostridium cellulosolvens, Clostridium cellulovorans, Clostridium thermocellum, Bacteroides cellulosolvens, and Acetivibrio cellulolyticus Gliricidia sp., Albizia sp., or Parthenium sp. Cupriavidus basilensis, Cupriavidus campinensis, Cupriavidus gilardi, Cupriavidus laharsis, Cupriavidus metallidurans, Cupriavidus oxalaticus, Cupriavidus pauculus, Cupriavidus pinatubonensis, Cupriavidus respiraculi, Cupriavidus taiwanensis, Oligotropha carboxidovorans, Thiobacillus sp., Thiobacillus denitrificans, Thiobacillus thioxidans, Thiobacillus ferrooxidans, Thiobacillus concretivorus, Acidithiobacillus albertensis, Acidithiobacillus caldus, Acidithiobacillus cuprithermicus, Rhodopseudomonas, Rhodopseudomonas palustris, Rhodobacter sphaeroides, Rhodopseudomonas capsulate, Rhodopseudomonas acidophila, Rhodopseudomonas viridis, Desulfotomaculum, Desulfotomaculum acetoxidans, Desulfotomaculum kuznetsovii, Desulfotomaculum nigrificans, Desulfotomaculum reducens, Desulfotomaculum carboxydivorans, Methanosarcina barkeri, Methanosarcina acetivorans, Moorella thermoacetica, Carboxydothermus hydrogenoformans, Rhodospirillum rubrum, Acetobacterium woodii, Butyribacterium methylotrophicum, Clostridium autoethanogenum, Clostridium ljungdahlii, Eubacterium limosum, Oxobacter pfennigii, Peptostreptococcus productus, Rhodopseudomonas palustris P4, Rubrivivax gelatinosus, Citrobacter sp Y19, Methanosarcina acetivorans C2A, Methanosarcina barkeri, Desulfosporosinus orientis, Desulfovibrio desulfuricans, Desulfovibrio vulgaris, Moorella thermoautotrophica, Carboxydibrachium pacificus, Carboxydocella thermoautotrophica, Thermincola carboxydiphila, Thermolithobacter carboxydivorans, Thermosinus carboxydivorans, Methanothermobacter thermoautotrophicus, Desulfotomaculum carboxydivorans, Desulfotomaculum kuznetsovii, Desulfotomaculum nigrificans, Desulfotomaculum thermobenzoicum subsp. thermosyntrophicum, Syntrophobacter fumaroxidans, Clostridium acidurici, Desulfovibrio africanus, C. pasteurianum, C. pasteurianum DSM 525, Paenibacillus polymyxa, Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Arthrospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phylariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis, Zygonium, Chloroflexus, Chloronema, Oscillochloris, Heliothrix, Herpetosiphon, Roseiflexus, Thermomicrobium, Chlorobium, Clathrochloris, Prosthecochloris, Allochromatium, Chromatium, Halochromatium, Isochromatium, Marichromatium, Rhodovulum, Thermochromatium, Thiocapsa, Thiorhodococcus, Thiocystis, Phaeospirillum, Rhodobaca, Rhodobacter, Rhodomicrobium, Rhodopila, Rhodopseudomonas, Rhodothalassium, Rhodospirillum, Rodovibrio, Roseospira, Nitrobacteraceae sp., Nitrobacter sp., Nitrospina sp., Nitrococcus sp., Nitrospira sp., Nitrosomonas sp., Nitrosococcus sp., Nitrosospira sp., Nitrosolobus sp., Nitrosovibrio sp., Thiovulum sp., Thiobacillus sp., Thiomicrospira sp., Thiosphaera sp., Thermothrix sp., Hydrogenobacter sp., Siderococcus sp., Aquaspirillum sp. Methanobacterium sp., Methanobrevibacter sp., Methanothermus sp., Methanococcus sp., Methanomicrobium sp., Methanospirillum sp., Methanogenium sp., Methanosarcina sp., Methanolobus sp., Methanothrix sp., Methanococcoides sp., Methanoplanus sp., Thermoproteus sp., Pyrodictium sp., Sulfolobus sp., Acidianus sp., Bacillus subtilis, Saccharomyces cerevisiae, Streptomyces sp., Ralstonia sp., Rhodococcus sp., Corynebacteria sp., Brevibacteria sp., Mycobacteria sp., oleaginous yeast, Arabidopsis thaliana, Panicum virgatum, Miscanthus giganteus, Zea mays (plants), Botryococcus braunii, Chlamydomonas reinhardtii and Dunaliela salina (algae), Synechococcus sp PCC 7002, Synechococcus sp. PCC 7942, Synechocystis sp. PCC 6803, Thermosynechococcus elongatus BP-1 (cyanobacteria), Chlorobium tepidum (green sulfur bacteria), Chloroflexus auranticusl, Chromatium tepidum and Chromatium vinosum (purple sulfur bacteria), Rhodospirillum rubrum, Rhodobacter capsulatus, and Rhodopseudomonas palusris (purple non-sulfur bacteria).

It is claimed:

1. A process for bioconverting a substrate in a fluid to a bioproduct comprising:
   a. contacting said fluid with a biocatalyst containing bioactive material capable of bioconverting said substrate to said bioproduct for a time sufficient for the up-take of at least a portion of said substrate into the biocatalyst and provide a loaded biocatalyst, said biocatalyst comprising (i) a solid structure of a hydrated hydrophilic polymer defining an interior structure having a plurality of interconnected major cavities having a smallest dimension of between about 5 and 100 microns and a Hydration Expansion Volume, which is calculated in volume percent, of about 1000 or more, and (ii) bioactive material substantially irreversibly retained therein;
   b. thereafter contacting the biocatalyst with an aqueous medium to facilitate metabolic activity; and
   c. thereafter using said biocatalyst in step (a), wherein the loaded biocatalyst in step (a) is maintained in at least one of steps (a) and (b) under metabolic conditions for a time sufficient to bioconvert at least a portion of the substrate to the bioproduct.

2. The process of claim 1 wherein the fluid is liquid.

3. The process of claim 1 wherein the fluid is gaseous.

4. The process of claim 1 wherein the bioactive material comprises microorganisms.

5. The process of claim 4 wherein the biocatalyst has a Hydration Expansion Volume of at least 5000 percent.

6. A process for bioconverting a substrate in a fluid to a bioproduct comprising:
   a. contacting said fluid with biocatalyst containing microorganisms capable of bioconverting said substrate to said bioproduct for a time sufficient for the up-take of at least a portion of said substrate into the biocatalyst and provide a loaded biocatalyst, said biocatalyst comprising (i) a solid structure of a hydrated hydrophilic polymer defining an interior structure having a plurality of interconnected major cavities having a smallest dimension of between about 5 and 100 microns and a Hydration Expansion Volume, which is calculated in volume percent, of about 1000 or more, and (ii) microorganisms substantially irreversibly retained therein;
   b. thereafter contacting the biocatalyst with an aqueous medium to facilitate metabolic activity; and
   c. thereafter using said biocatalyst in step (a), wherein the loaded biocatalyst in step (a) is maintained in at least one of steps (a) and (b) under metabolic conditions for a time sufficient to bioconvert at least a portion of the substrate to bioproduct.

7. The process of claim 6 wherein the fluid is gaseous.

8. The process of claim 6 wherein the fluid is a non-aqueous liquid.

* * * * *